United States Patent
Zhou et al.

(10) Patent No.: US 10,945,695 B2
(45) Date of Patent: Mar. 16, 2021

(54) APPARATUS AND METHOD FOR DUAL-ENERGY COMPUTED TOMOGRAPHY (CT) IMAGE RECONSTRUCTION USING SPARSE KVP-SWITCHING AND DEEP LEARNING

(71) Applicant: CANON MEDICAL SYSTEMS CORPORATION, Otawara (JP)

(72) Inventors: Jian Zhou, Buffalo Grove, IL (US); Yan Liu, Vernon Hills, IL (US); Zhou Yu, Glenview, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 108 days.

(21) Appl. No.: 16/231,189

(22) Filed: Dec. 21, 2018

(65) Prior Publication Data
US 2020/0196973 A1   Jun. 25, 2020

(51) Int. Cl.
*A61B 6/00* (2006.01)
*G06T 11/00* (2006.01)
(Continued)

(52) U.S. Cl.
CPC .......... *A61B 6/5258* (2013.01); *A61B 6/032* (2013.01); *A61B 6/482* (2013.01); *A61B 6/5205* (2013.01);
(Continued)

(58) Field of Classification Search
CPC ....... A61B 6/5258; A61B 6/032; A61B 6/482; A61B 6/5205; G06N 20/00; G06N 3/084;
(Continued)

(56) References Cited

U.S. PATENT DOCUMENTS

| 6,999,549 B2 | 2/2006 | Sabol et al. |
| 2016/0093048 A1* | 3/2016 | Cheng .................. G06K 9/6289 382/131 |

(Continued)

FOREIGN PATENT DOCUMENTS

| CN | 107203989 A | 9/2017 |
| WO | WO 2017/223560 A1 | 12/2017 |
| WO | WO 2018/126396 A1 | 7/2018 |

OTHER PUBLICATIONS

Wenkun Zhang, et al. "Image Domain Dual Material Decomposition for Dual Energy using Butterfly Network".
(Continued)

*Primary Examiner* — Khai M Nguyen
(74) *Attorney, Agent, or Firm* — Oblon, McClelland, Maier & Neustadt, L.L.P.

(57) ABSTRACT

A deep learning (DL) network reduces artifacts in computed tomography (CT) images based on complementary sparse-view projection data generated from a sparse kilo-voltage peak (kVp)-switching CT scan. The DL network is trained using input images exhibiting artifacts and target images exhibiting little to no artifacts. Another DL network can be trained to perform image-domain material decomposition of the artifact-mitigated images by being trained using target images in which beam hardening is corrected and spatial variations in the X-ray beam are accounted for. Further, material decomposition and artifact mitigation can be integrated in a single DL network that is trained using as inputs reconstructed images having artifacts and as targets material images without artifacts with beam-hardening corrections, etc. Further, the target material images can be transformed using a whitening transform to decorrelate noise.

20 Claims, 25 Drawing Sheets

(51) Int. Cl.
   G06N 3/08    (2006.01)
   G06N 20/00   (2019.01)
   A61B 6/03    (2006.01)
   G06T 5/00    (2006.01)
   G06T 5/50    (2006.01)

(52) U.S. Cl.
   CPC ............. *G06N 3/084* (2013.01); *G06N 20/00* (2019.01); *G06T 5/001* (2013.01); *G06T 5/50* (2013.01); *G06T 11/008* (2013.01); *G06T 2207/10081* (2013.01); *G06T 2207/20081* (2013.01); *G06T 2207/20084* (2013.01)

(58) Field of Classification Search
   CPC ......... G06T 5/001; G06T 5/50; G06T 11/008; G06T 2207/10081; G06T 2207/20081; G06T 2207/20084
   See application file for complete search history.

(56) References Cited

U.S. PATENT DOCUMENTS

| | | | |
|---|---|---|---|
| 2017/0294034 A1* | 10/2017 | Zhou | G06T 11/008 |
| 2017/0362585 A1* | 12/2017 | Wang | G06N 3/08 |
| 2018/0018757 A1 | 1/2018 | Suzuki | |
| 2018/0099152 A1 | 4/2018 | Nioutsikou | |
| 2019/0066346 A1* | 2/2019 | Ye | G06T 11/006 |
| 2019/0104940 A1* | 4/2019 | Zhou | G06T 11/008 |
| 2019/0371018 A1* | 12/2019 | Ye | G06T 11/008 |

OTHER PUBLICATIONS

Tobias Wurfl, et al. "Deep Learning Computed Tomography: Learning Projection-Domain Weights from Image Domain in Limited Angle Problems", IEEE Transactions on Medical Imaging Special Issue on Machine Learning for Image Reconstruction, http://dx.doi.org/10.1109/TMI.2018.2833499.

Hu Chen, et al. "Low-Dose CT with a Residual Encoder-Decoder Convolutional Neural Network (RED-CNN)", IEEE 2017.

Eunhee Kang, et al. "Wavelet Domain Residual Network (WavResNet) for Low-Dose X-Ray CT Reconstruction", 2017.

Qingsong Yang, et al. "CT Image Denoising with Perceptive Deep Neural Networks", The 14$^{th}$ International Meeting on Fully 3D Image Reconstruction in Radiology and Nuclear Medicine, 2017.

Han Yo Seob, et al. "Deep Residual Learning Approach for Sparse-View CT Reconstruction", The 14$^{th}$ International Meeting on Fully 3D Image Reconstruction in Radiology and Nuclear Medicine, 2017.

Heyi Li, et al. "Low-Dose CT Streak Artifacts Removal Using Deep Residual Neural Network", The 14th International Meeting on Fully 3D Image Reconstruction in Radiology and Nuclear Medicine, 2017.

Yanye Lu, et al. "Material Decomposition Using Ensemble Learning for Energy-Resolved Computed Tomography", The 14th International Meeting on Fully 3D Image Reconstruction in Radiology and Nuclear Medicine, 2017.

Extended European Search Report dated May 4, 2020 in European Patent Application No. 19216172.7, 10 pages.

Kang, E., et al., "A Deep Convolutional Neural Network using Directional Wavelets for Low-dose X-ray CT Reconstruction", ARXIV.org, Cornell University Library, Oct. 31, 2016, XP081364425, pp. 1-32.

Zhang, H., et al., "Image Prediction for Limited-angle Tomography via Deep Learning with Convolutional Neural Network", Retrieved from the Internet: URL: https://arxiv.org/ftp/arxiv/papers/1607/1067.08707.pdf, Jul. 29, 2016, XP055451427, 21 pages.

\* cited by examiner

APPARATUS AND METHOD FOR DUAL-ENERGY COMPUTED TOMOGRAPHY (CT) IMAGE RECONSTRUCTION USING SPARSE KVP-SWITCHING AND DEEP LEARNING

FIELD

This disclosure relates to using deep learning (DL) networks to reconstruct a computed tomography (CT) image from dual-energy (DE) sparse kilo-voltage peak (kVp)-switching projection data.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Computed tomography (CT) systems and methods are widely used, particularly for medical imaging and diagnosis. CT systems generally create images of one or more sectional slices through a subject's body. A radiation source, such as an X-ray tube, irradiates the body from one side. The attenuation of the radiation that has passed through the body is measured by processing electrical signals received from the detector, which are then used to reconstruct an image of the body by performing an inverse Radon transformation (or an equivalent thereof).

Originally, energy-integrating detectors were used to measure CT projection data, but more recently, photon-counting detectors have become a feasible alternative to conventional energy-integrating detectors. Photon-counting detectors (PCDs) have many advantages including being able to perform spectral CT. To obtain the spectral nature of the transmitted X-ray data, the photon-counting detectors split the X-ray beam into its component energies or spectrum bins and count a number of photons in each of the bins. Since spectral CT involves the detection of transmitted X-rays at two or more energy levels, spectral CT generally includes dual-energy CT by definition.

Spectral and dual-energy CT are advantageous because they can be used to perform material decompositions, whereby bone can be distinguished from soft tissues in the body, providing more clinical information for doctors and medical clinicians. Various configurations can be used for spectral imaging in CT. In general, the spectral CT configurations breakdown into two types, (i) generating different energy spectra at X-ray source in combination with energy integrating detector (e.g., fast kilo-voltage peak (kVp)-switching, and dual source configurations), and (ii) a broad-energy-spectrum X-ray source together with an energy discriminating/resolving detector.

More particularly, there are four spectral CT configurations of practical significance: PCD spectrally resolving detectors, dual-layer detectors, dual source and detector systems, and fast kVp-switching. For example, the PCDs discussed above can be used as energy resolving detectors with a broad-spectrum X-ray source. Another type of energy resolving detector uses various X-ray energy filters arranged in front of respective energy integrating detectors, such that the filters perform the function of separating the detected X-rays into different energy bands (e.g., a dual-layer detector that can separate photons by energy). In a third spectral CT configuration, dual X-ray sources are arranged opposite respective detectors, each source-detector pairing forming its own CT scanner system without overlapping with or interfering with the other (e.g., being arranged at right angles) and each source-detector pairing operating at a different X-ray spectrum than the other. With this arrangement, two CT scans with two different X-ray spectra can be simultaneously performed. In a forth configuration, a single integrating source can be used with an X-ray that uses fast kVp-switching to rapidly alternate between a high-energy X-ray spectrum and low-energy X-ray spectrum as the view angle of the CT scanner rotates around the patient. However, each of these four alternatives for spectral/dual-energy CT has its own unique pitfalls and shortcomings.

For example, photon-counting detectors (PCDs) are susceptible to pulse pileup (i.e., multiple X-ray detection events occurring at a single detector can within the detector's time response). Further, efforts to curb pileup by making the PCDs smaller in cross-sectional area are limited by tradeoffs due to increased susceptibility to charge migration/sharing and k-escape.

In the dual-layer detector approach, the combination of scintillators and photo-multiplier tubes suffer from low-energy noise and from being poorly optimized to achieve out-of-band energy suppression. Further, energy separation is degraded by the significant overlap between the two readout spectra.

The dual-source and dual-detector configuration suffers from being expensive and from cross-scatter effects.

The fast kVp-switching configuration is also expensive due to the additional costs associated with an ultra-high frequency generator and parallel data acquisitionsystems (DASs) used to acquire in parallel the high-energy and lose-energy projection data.

Accordingly, a better spectral CT approach is desired that overcomes the above-identified deficiencies in the related approaches.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1:
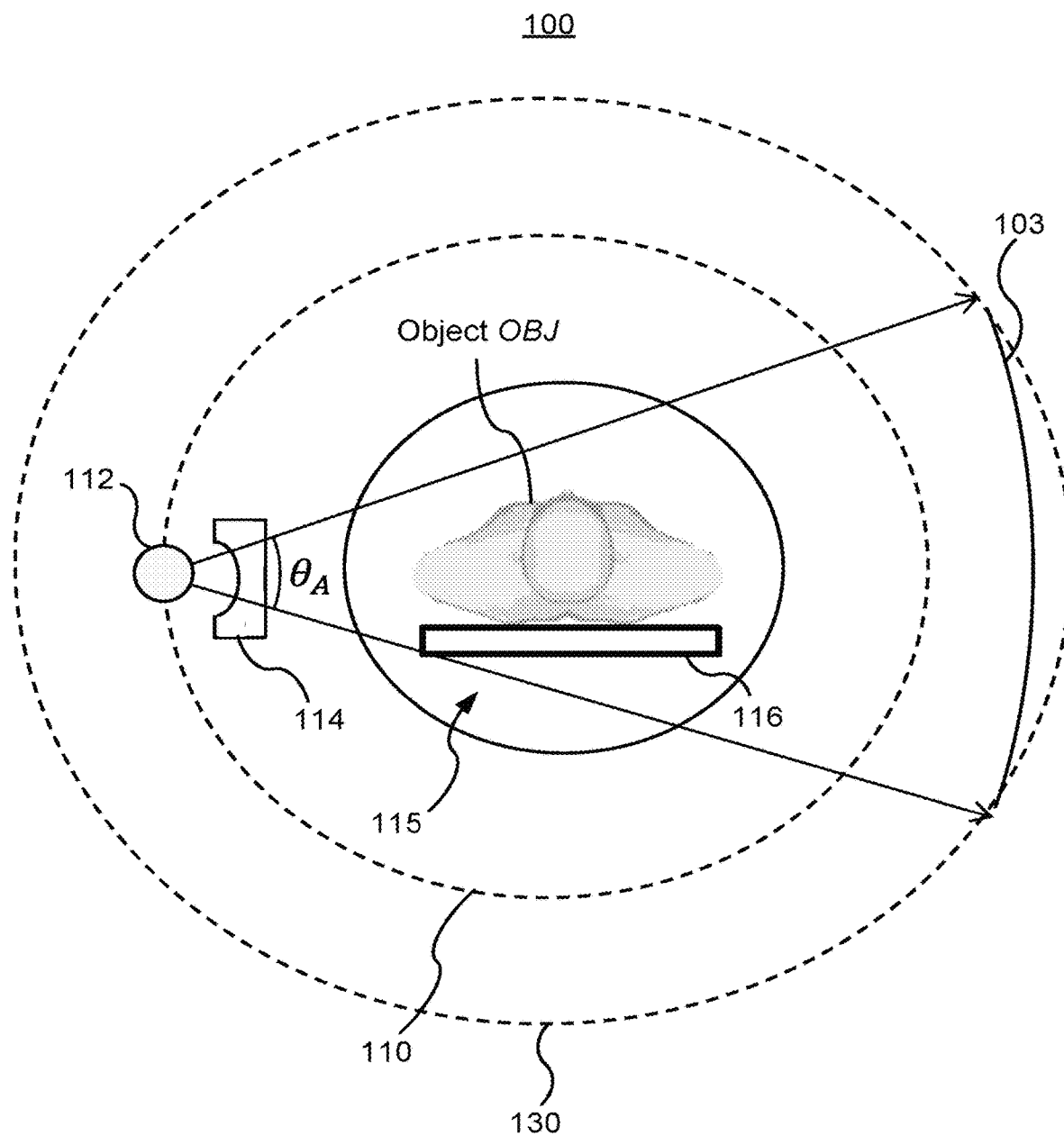
FIG. 1 shows a schematic diagram of an arrangement of an X-ray source and detector in a computed tomography (CT) scanner, according to one implementation.

The methods and apparatus described herein overcome the above-identified deficiencies of other spectral and dual-energy (DE) computed tomography (CT) approaches. These deficiencies are overcome by applying reconstructed images from sparse-view projection data, which is generated using sparse kVp-switching, to a deep learning (DL) artificial neural network (ANN) to remove artifacts from and decompose the spectral reconstructed images into material component images.

As discussed above, related approaches to spectral CT suffer from various deficiencies, including, e.g., higher costs and/or degraded image quality.

For example, higher cost is a deficiency in both fast kVp-switching and dual/detector-source systems. The methods described herein use kVp-switching but, in contrast to fast kVp-switching systems, the kilo-voltage peak (kVp) applied across the X-ray tube of the source is switched slowly (i.e., the kVp switching is sparse, resulting in sparse view projection data for both low- and high-kVp values). That is, rather than switching between low- and high-kVp values for each change of the projection angle (view), the kVp-switching used herein is sparse, meaning the kVp-switching is performed less frequently, such that a given kVp setting is maintained as the CT scanner rotates through several projection angle before switching to the other kVp setting. Accordingly, after switching to a high kVp setting the X-ray source maintains the high kVp voltage while the scanner rotates through and acquires projection images at many projection angles before switching back to a low kVp setting, which is then maintained through the next several projection angles, and so forth. In this way a single data acquisition system (DAS) can be used, and simpler, less expensive hardware is sufficient to switch the voltage across the X-ray tube given the slower rate of kVp-switching.

The methods described herein avoid the deficiencies of photon counting detectors (PCDs) such as pileup because the methods described herein use energy integrating detectors, rather than PCDs. Further, the methods described herein overcome the deficiencies of dual-layer detectors because the two energy spectra are achieved by modulating/switching the voltage applied across the X-ray source, rather than by filtering the X-ray energies at the X-ray detector.

The methods described herein use sparse-kVp-switching dual-energy CT (DECT) system to generate sparse view projection data for a low- and high-energy X-ray spectra, respectively. Because the kVp-switching is performed less frequently than in fast kVp-switching, the methods described herein can be performed using a high-frequency generator (as opposed to the ultra-high frequency generator used for fast kVp-switching). Further, the sparse kVp-switching can be performed using a single sequential DAS (as opposed to the parallel DASs used for fast kVp-switching).

One of the major challenges for the the sparse kVp-switching approach to DECT and is that the sparse view data presents challenges with respective to the image quality and material decomposition of the reconstructed images. More particularly, for sparse kVp-switching projection data, it has proven difficult to develop an efficient reconstruction algorithm that is not susceptible to streak artifacts, beam hardening, and other effects degrading the image quality. On the one hand, analytical reconstruction methods such as filtered back-projection (FBP) can be efficient, but, when they are applied to sparse projection data, they generate reconstructed images that suffer from streak artifacts. On the other hand, iterative reconstruction methods, when applied to sparse projection data, can result in degraded spatial resolution and degraded noise texture due to the lower dose of X-rays at each kVp setting. The "kVp" is the peak kilovoltage (kV) applied between the anode and cathode of an X-ray tube source. Another challenge with sparse kVp-switching projection data is that the trajectories traced by the X-rays to the detector pixels are different between the two kVp setting, rendering sinogram-domain material decomposition infeasible. However, image-domain material decomposition has its own set of difficulties, including, e.g., beam hardening corrections and spatial variations in the energy spectrum of the X-ray beam (e.g., due to different paths through a bow tie filter).

To address the above challenges, the methods described herein use a deep learning (DL) approach to mitigate artifacts in images reconstructed sparse-view projection data acquired using sparse kVp-switching DECT system. Further, the methods described herein use the deep learning (DL) approach also for image-domain material decomposition.

Referring now to the drawings, wherein like reference numerals designate identical or corresponding parts throughout the several views, FIG. 1 shows a configuration of an X-ray source and detector in computed tomography (CT) scanner having energy-integrating detectors arranged in a third-generation geometry. Illustrated in FIG. 1 is a non-limiting example of relative positions among an imaged object OBJ resting on a table 116, an X-ray source 112, a collimator/filter 114, and a pixelated X-ray detector 103, which includes an array of individual detector elements (i.e., pixels).

In one implementation, the X-ray source 112, the collimator/filter 114 are fixedly connected to a rotational component 110 that is rotatably connected to a gantry. For example, the rotational component 110 can be an annular ring configured to rotate within a gantry while the object OBJ remains fixed in space on the table 116, or, alternatively, in a helical scan the table can be translated along the bore of the gantry while the X-ray source 112 and the X-ray detector 103 are rotated around the bore of the gantry. The gantry of the CT scanner also includes an open aperture 115 within the bore, which can be centered at the iso-center of the rotational component 110. The open aperture 115 enables the object OBJ to be placed in a projection plane of the X-rays from the X-ray source. In certain implementations, the X-ray detector 103 is fixedly connected to another rotational component 130 that is rotatably connected to the gantry. In a rotate/rotate configuration, the rotational component 110 and the rotational component 130 can rotate in unison, maintaining the X-ray detector 103 diametrical opposed to the X-ray source 112 to obtain projection data of the object OBJ at a progression of projection angles (i.e., views). Sinograms are created by arranging the projection data with projection angles arranged along one axis and the spatial dimensions of the projection data arranged along the other axes. The projection data (sinograms) can be used to reconstruct a cross-sectional image of the object OBJ.

In spectral CT, projection data having multiple energy components is used to represent projective measurements of the object OBJ. These projective measurements are made at a series of angles enabling conventional CT image reconstruction methods similar to non-spectral CT. However, unlike non-spectral CT, spectral CT generates additional information (i.e., spectral attenuation information) enabling a decomposition of the projective measurements into material components. Setting aside k-edge methods, the number of materials is usually two, based on the unique spectral signatures of X-ray attenuation due to Compton scattering and photoelectric attenuation, respectively. That is, the spectral differences between the X-ray attenuation for two material components arise from the different ratios of Compton scattering to photoelectric attenuation they exhibit e (e.g., the X-ray attenuation due to a high-Z material like iodine is comprised of a different ratio of Compton scattering to photoelectric attenuation than a low-Z material like water).

Mapping the projection data from the spectral domain to the material domain can be performed either in the sinogram-domain (i.e., before the image reconstruction process) or in the image-domain (i.e., after the image reconstruction process). However, to be performed in the sinogram (projection) domain, the projection data should include identical (or nearly identical) X-ray trajectories for each of the dual-energy components. In fast kVp-switching, this achieved because the CT scanner has rotated very little between adjacent high-kV and low-kV projection views. However, for sparse kVp-switching the difference between X-ray trajectories becomes large between the projection views in the middle of a long sequence of images acquired at the same low- or high-kVp settings on the X-ray tube.

The attenuation of X-rays in biological materials is dominated by two physical processes (i.e., photoelectric absorption and Compton scattering). Thus, the attenuation coefficient as a function of energy can be approximated by the decomposition $$\mu(E,x,y)=\mu_{PE}(E,x,y)+\mu_c(E,x,y),$$

wherein $\mu(E, x, y)$ is the photoelectric attenuation and $\mu_c(E, x, y)$ is the Compton attenuation. Alternatively, this attenuation coefficient can be rearranged into a decomposition of a high-Z material (i.e., material 1) and a low-Z material (i.e., material 2) to become $$\mu(E,x,y)=\mu_1(E)c_1(x,y)+\mu_2(E)c_2(x,y),$$

wherein c, (x, y) and $c_2$ (x, y) are, respectively correspond to a first and second material component. Material decomposition is the process of solving from the c, (x, y) and $c_2$ (x, y) that best approximate with measured/reconstructed attenuation spectra.

Figure 2A:
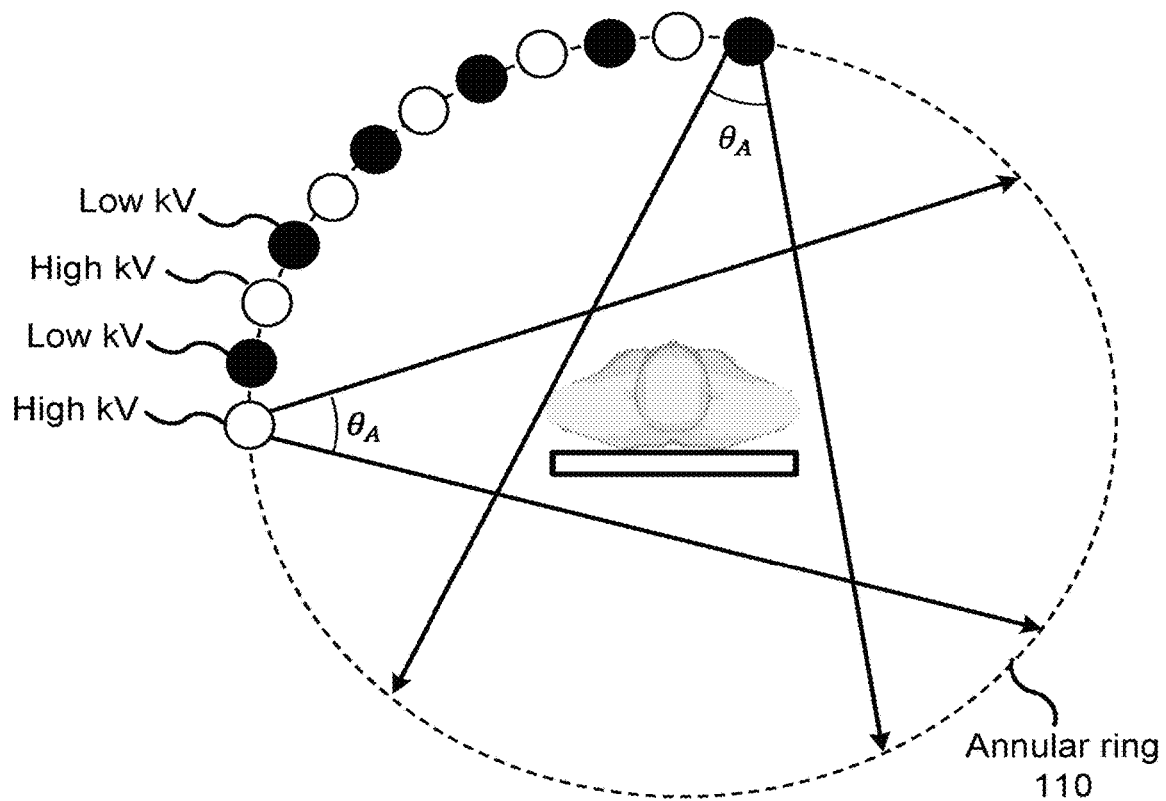
FIG. 2A shows an example of view angles/positions of an X-ray source for fast kVp-switching, according to one implementation.
Figure 2B:
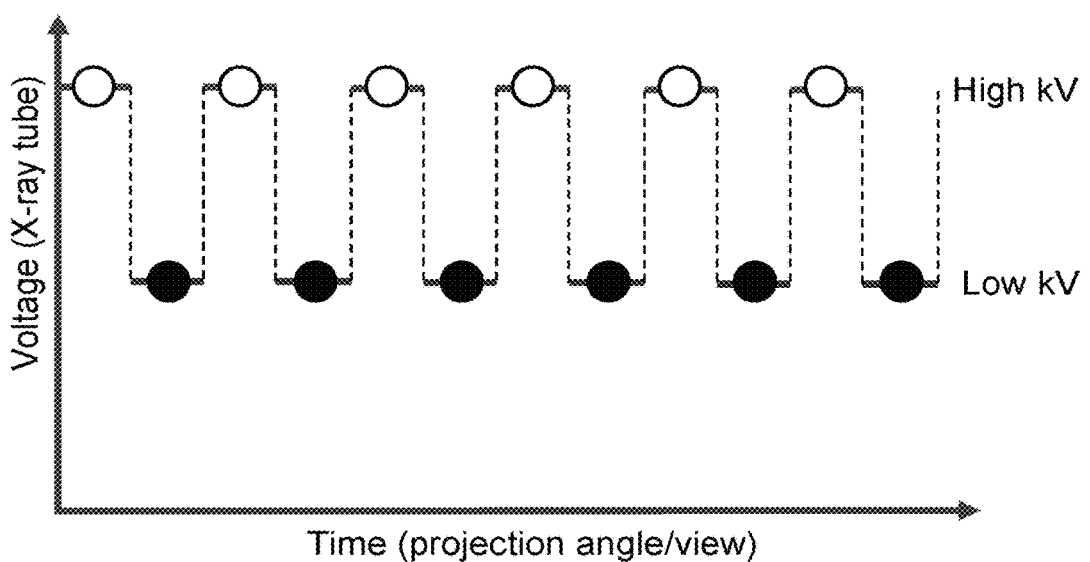
FIG. 2B shows an example of kilo-voltage peak values as a function of time for fast kVp-switching, according to one implementation.

FIGS. 2A and 2B show diagrams of an implementation of fast kVp-switching. The kVp setting on the X-ray tube is changed for each projection angle. In FIG. 2A, the locations of the X-ray source for acquisitions of a projection image using a high-kVp (low-kVp) setting are indicated by the white (black) circles. In FIG. 2B, the voltage applied to the X-ray tube is shown as a function of time, with the time and voltage for projection images acquired at the high-kVp (low-kVp) setting indicated by the white (black) circles.

Figure 3A:
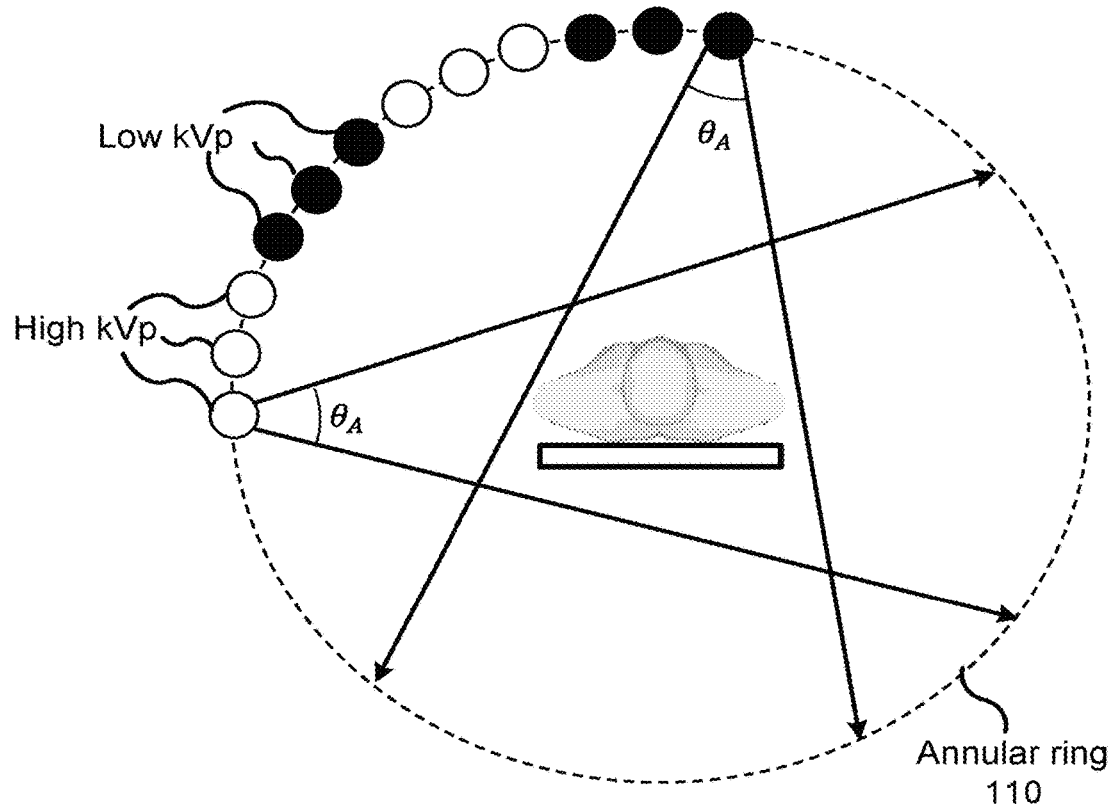
FIG. 3A shows an example of view angles/positions of an X-ray source for sparse kVp-switching, according to one implementation.
Figure 3B:
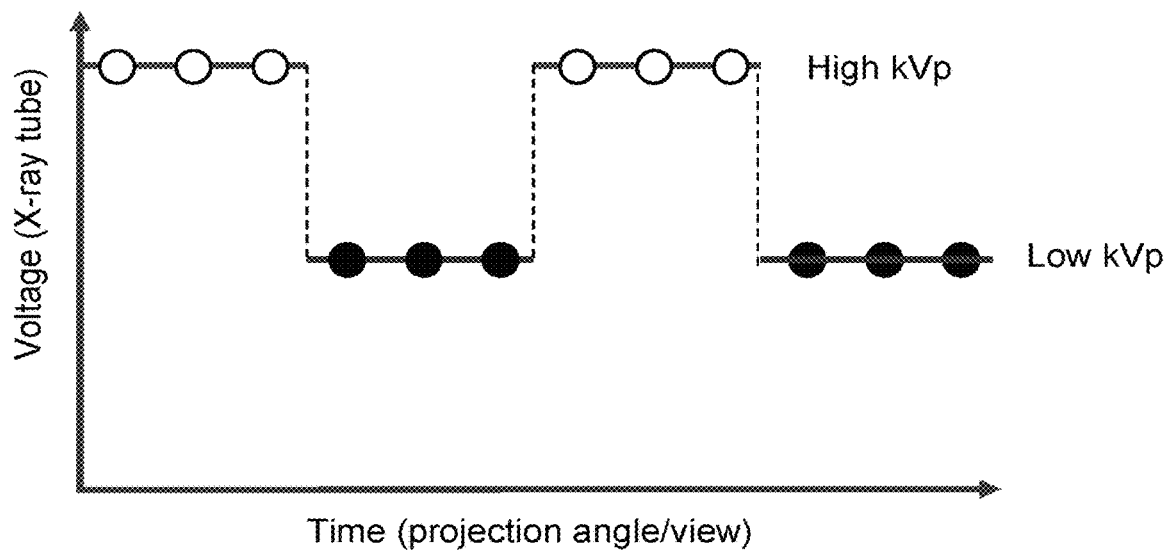
FIG. 3B shows an example of kilo-voltage peak values as a function of time for spars kVp-switching, according to one implementation.

FIGS. 3A and 3B show diagrams of an implementation of sparse kVp-switching. The kVp setting on the X-ray tube is changed only after a succession of N projection images at different projection angles have been acquired, where N is a number greater than one. In FIG. 3A, the locations of the X-ray source for acquisitions of a projection image using a high-kVp (low-kVp) setting are indicated by the white (black) circles. In FIG. 3B, the voltage applied to the X-ray tube is shown as a function of time, with the time and voltage for projection images acquired at the high-kVp (low-kVp) setting indicated by the white (black) circles.

In the non-limiting example of FIGS. 3A and 3B, N is three, but N can be any integer two or greater. Further, the number of successive projection images acquired at a given kVp setting does not need to be constant throughout a CT scan, and different intervals can be applied between different kVp settings (e.g., within a given CT scan, more projection images can be acquired at a high-kVp setting than at a low-kVp setting or vice versa), as would be understood by a person of ordinary skill in the art.

Figure 4:
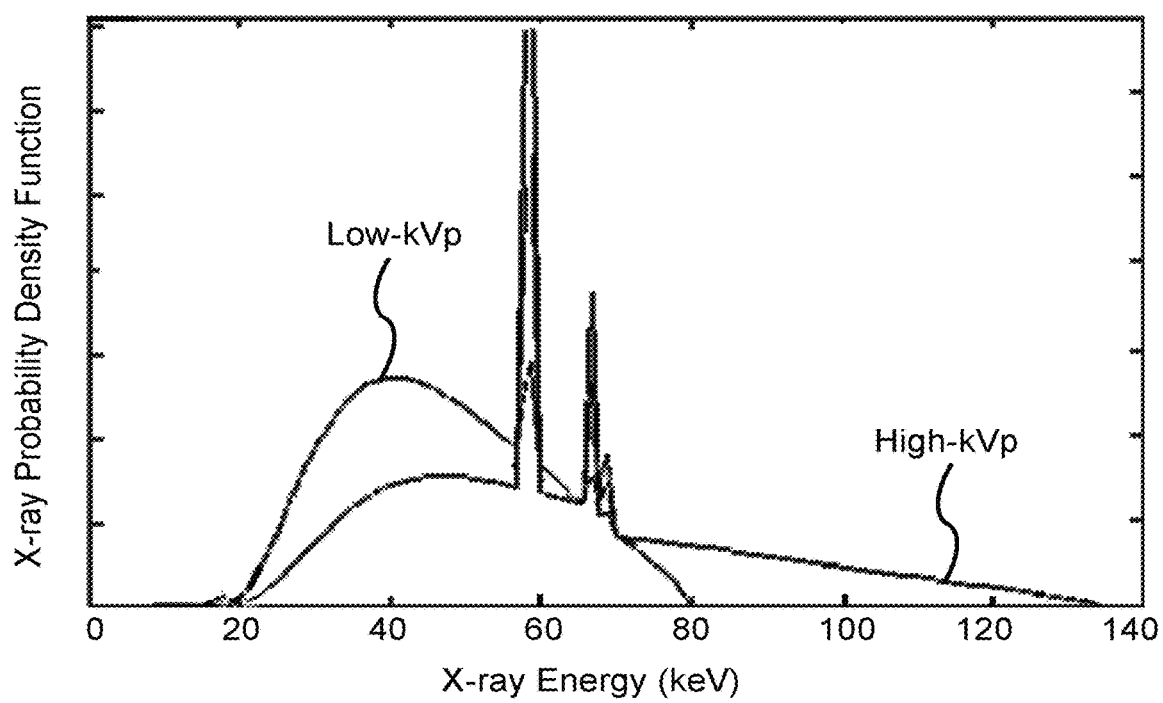
FIG. 4 shows a plot of a probability density function for an energy spectra of X-rays emitted at low- and high-kVp switching, according to one implementation.

The method of sparse kVp-switching is illustrated herein using the non-limiting example of a low-kVp setting of 80 kVp and a high-kVp setting of 135 kVp. For an X-ray tube, the X-ray spectrum is mainly controlled by the voltage (kVp) applied between the anode and cathode to accelerate the electrons before the electrons are suddenly stopped by colliding with the cathode, converting the kinetic energy of the electron into X-rays via a Bremsstrahlung radiation mechanism. By this process, different X-ray spectra can be produced by changing the voltage applied across of the X-ray tube. FIG. 4 shows the probability distribution of the X-ray energy produced with a low-kVp setting of 80 kVp and a high-kVp setting of 135 kVp, respectively.

Figure 5A:
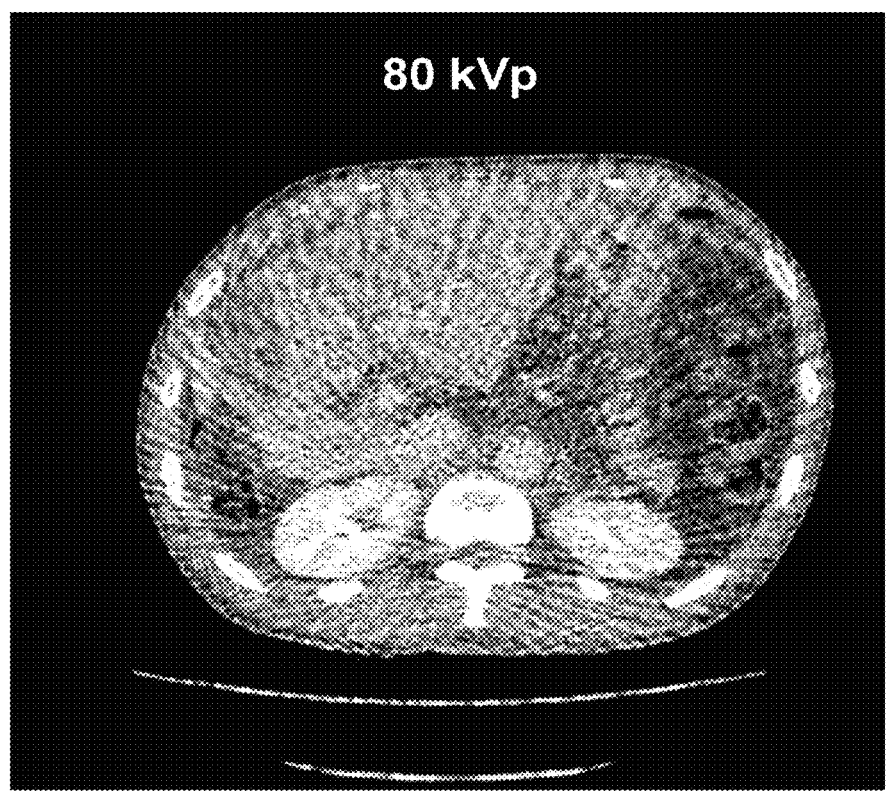
FIG. 5A shows an image reconstructed using an adaptive iterative dose reduction (AIDR) three-dimensional (3D) reconstruction method, the image being reconstructed from sparse kVp-switching projection data for a low-kVp value of 80 kVp, according to one implementation.
Figure 5B:
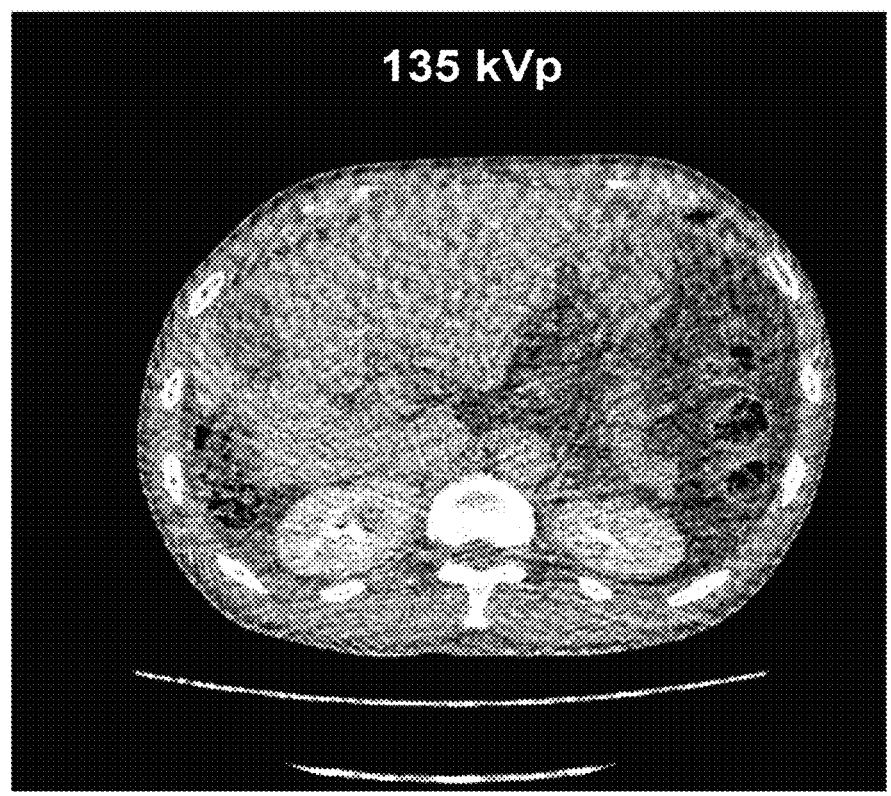
FIG. 5B shows an image reconstructed using an AIDR-3D method, the image being reconstructed from sparse kVp-switching projection data for a high-kVp value of 135 kVp, according to one implementation.
Figure 5C:
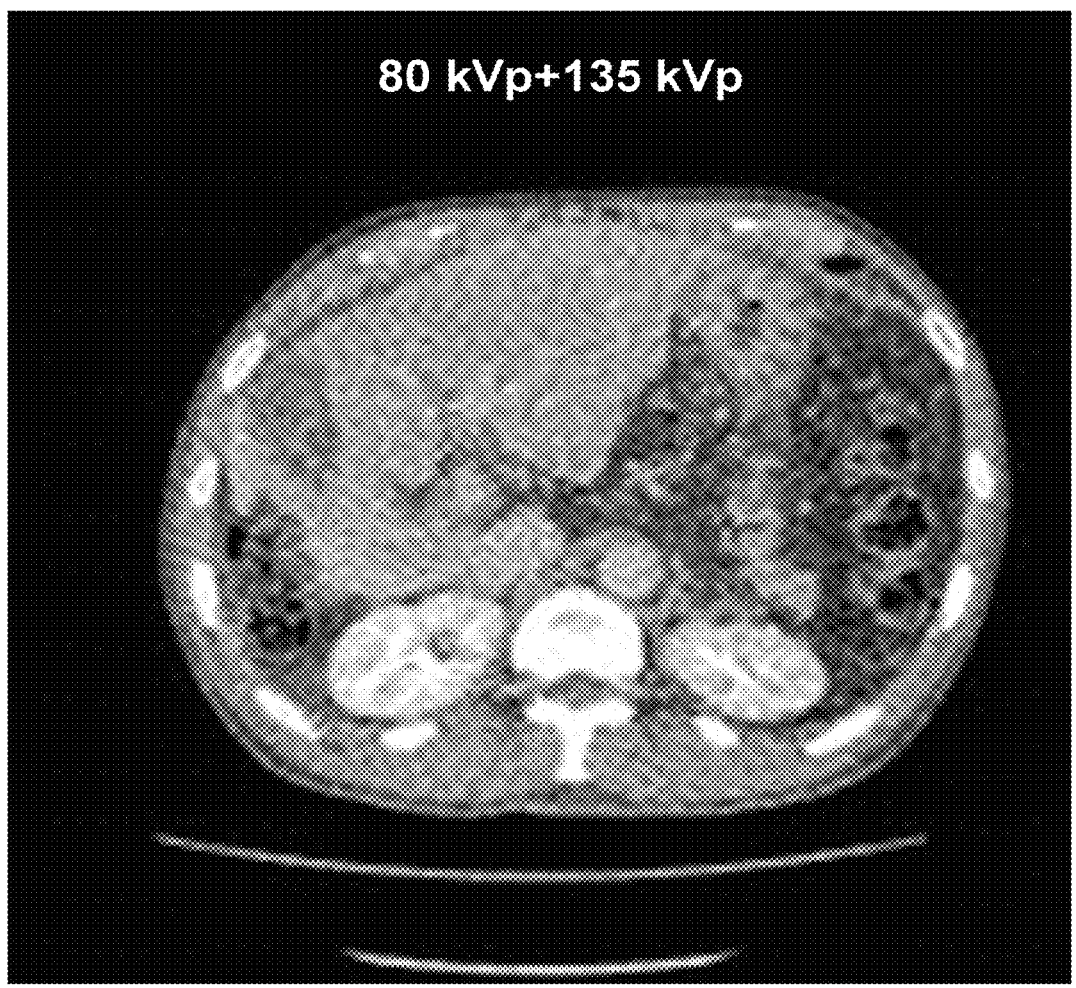
FIG. 5C shows a sum of the images in FIGS. 5A and 5B, according to one implementation.

As discussed above, a challenge of image reconstruction using projection data acquired using sparse kVp-switching is that the image quality tends to be degraded due to streak artifacts. For example, FIGS. 5A and 5B show examples of reconstructed images generated using FBP reconstruction with sparse kVp-switching projection data for 80 kVp and 135 kVp, respectively. The streak artifacts are clearly evident. Further, close inspection reveals that the streak artifacts tend to be complementary. That is, a bright streak in the 80 kVp image corresponds to a dark streak in the 135 kVp image, and vice versa. To illustrate this, FIG. 5C shows a sum of the 80 kVp image with the 135 kVp image. To a significant degree the bright streak artifacts in the 80 kVp image counteract the dark streak artifacts in the 135 kVp image. These streak artifacts can be understood as arising from the fact that the projection angles for the 80 kVp and 135 kVp projection data are complementary, as shown in FIG. 3A. For example, the sequences/intervals of projection angles for which the CT scanner is set to the High-kVp setting is the complement of and is mutually exclusive with the sequences/intervals of projection angles for which the CT scanner is set to the Low-kVp setting. Thus, the information from the two images can be combined to mitigate the streak artifacts.

The methods described herein use a DL-ANN to learn how to best to use the combined information from the respective low- and high-kVp reconstructed images to correct for the streak artifacts to generate high-quality images. In certain implementations, reconstructing images using an FBP reconstruction method and then applying the DL-ANN network for artifact and noise correction can be faster and yield comparable or better image quality than directly reconstructing a high-quality image using an iterative reconstruction method with an appropriately chosen regularizer (e.g., a total variation minimization (TV) regularization term).

Figure 6:
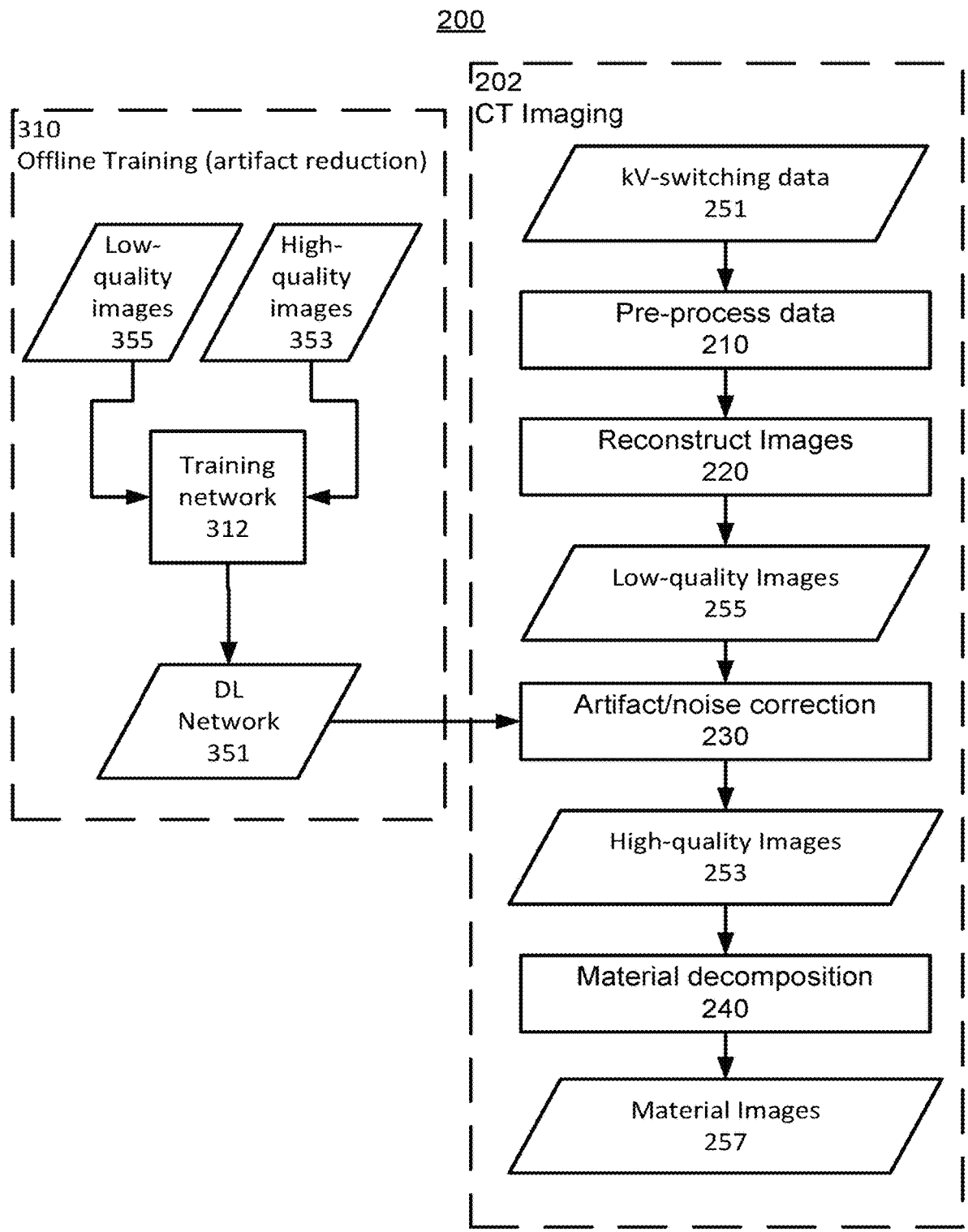
FIG. 6 shows an example of a flow diagram for training and using a deep learning (DL) artificial neural network (ANN) to correct artifacts in sparse kVp-switching projection data, according to one implementation.

FIG. 6 shows a flow diagram of a method 200 for sparse kVp-switching CT image reconstruction that includes a process 310 of training artifact-correction network 351, and includes a process 202 of applying the trained artifact-correction network 351 to correct sparse view reconstructed images 255 to ultimately generate high-quality material-basis images 257.

In process 310, a loss function is used to iteratively adjust parameters (e.g., weights and biases of convolutional and pooling layers) of the DL-ANN network 351 until stopping criteria are satisfied (e.g., convergence of the network coefficients/parameters to a predefined threshold) to generate the trained network 351. The loss function compares high-quality training data 353 (e.g., full-scan images at the respective kVp settings) to a result arising from applying a low-quality training data 355 (e.g., sparse kVp-switching images) to a current version of the DL-ANN network 351. Each pair of high-quality images (e.g., one high-quality image acquired at each of the two kVp settings) is combined with a corresponding pair of low-quality images generated by imaging the same object OBJ or phantom as imaged in the pair of high-quality images. The high-quality images can be referred to as the "target" or "label" and the low-quality images are referred to as the "input." The training data can include a large set of corresponding targets and inputs. The offline training can be performed in advance of a given CT scan (e.g., when a CT scanner is initially installed and calibrated), and the trained DL-ANN network 351 can be stored in memory until a CT scan is acquired and the image reconstruction is performed in step 210.

Figure 7A:
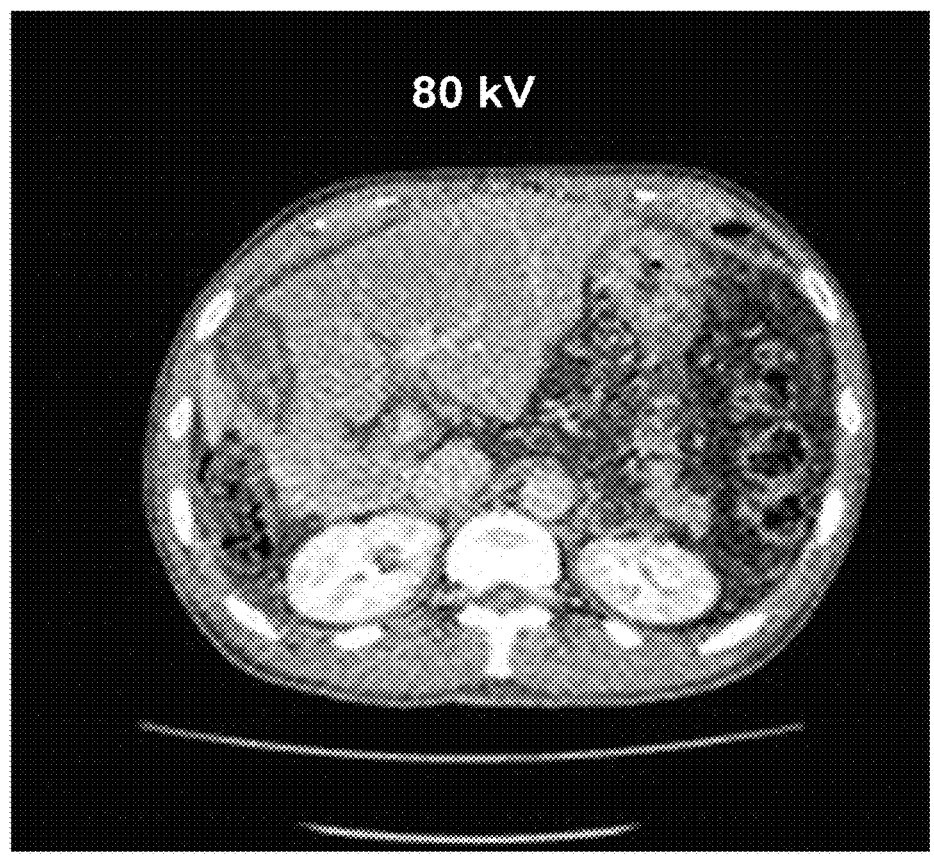
FIG. 7A shows an example of a high-quality image for full-view projection data acquired at 80 kVp to be paired with the image in FIG. 5A in a training data set, according to one implementation.
Figure 7B:
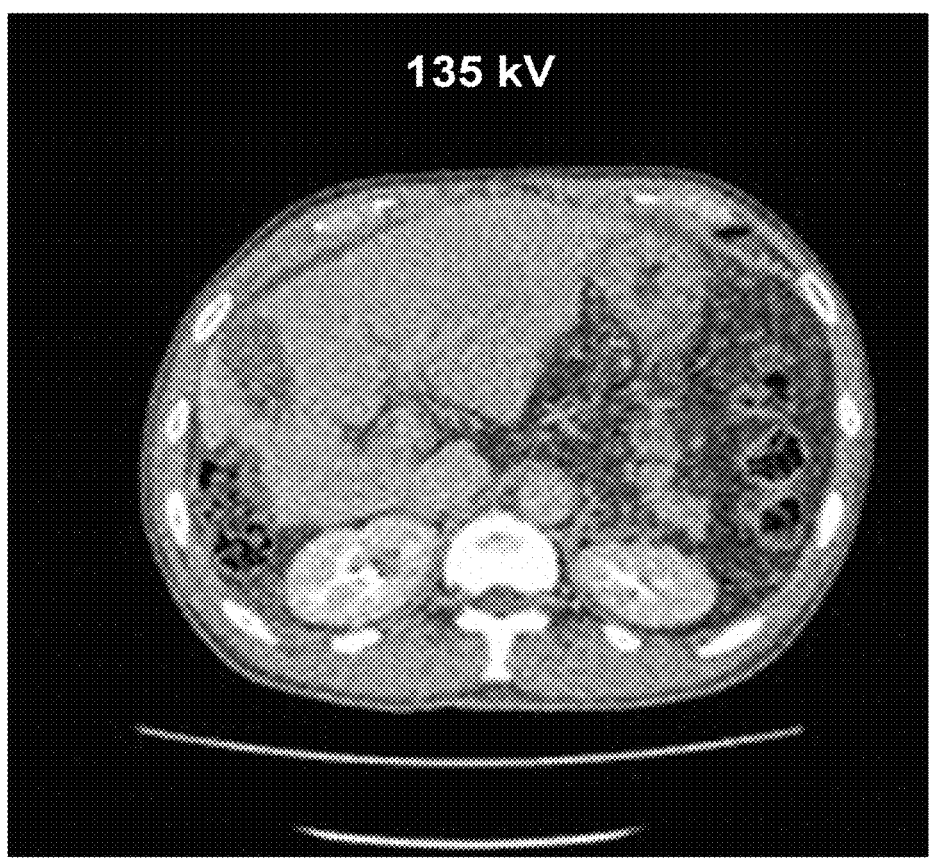
FIG. 7B shows an example of a high-quality image for full-view projection data acquired at 135 kVp to be paired with the image in FIG. 5B in a training data set, according to one implementation.

FIGS. 7A and 7B show examples of high-quality images generated at kVp settings of 80 kV and 135 kV, respectively. The high-quality images can be reconstructed using a full-view scan at each kVp setting, rather than using sparse-view projection data. Further, the high-quality images can be reconstructed using techniques that are known to produce better image quality (e.g., iterative reconstruction with regularization and denoising) The images in FIGS. 7A and 7B could be used as the target images in combination with the images in FIGS. 5A and 5B, which would be used as input images, to form part of a training data set that would be used to train a network 351.

Figure 8:
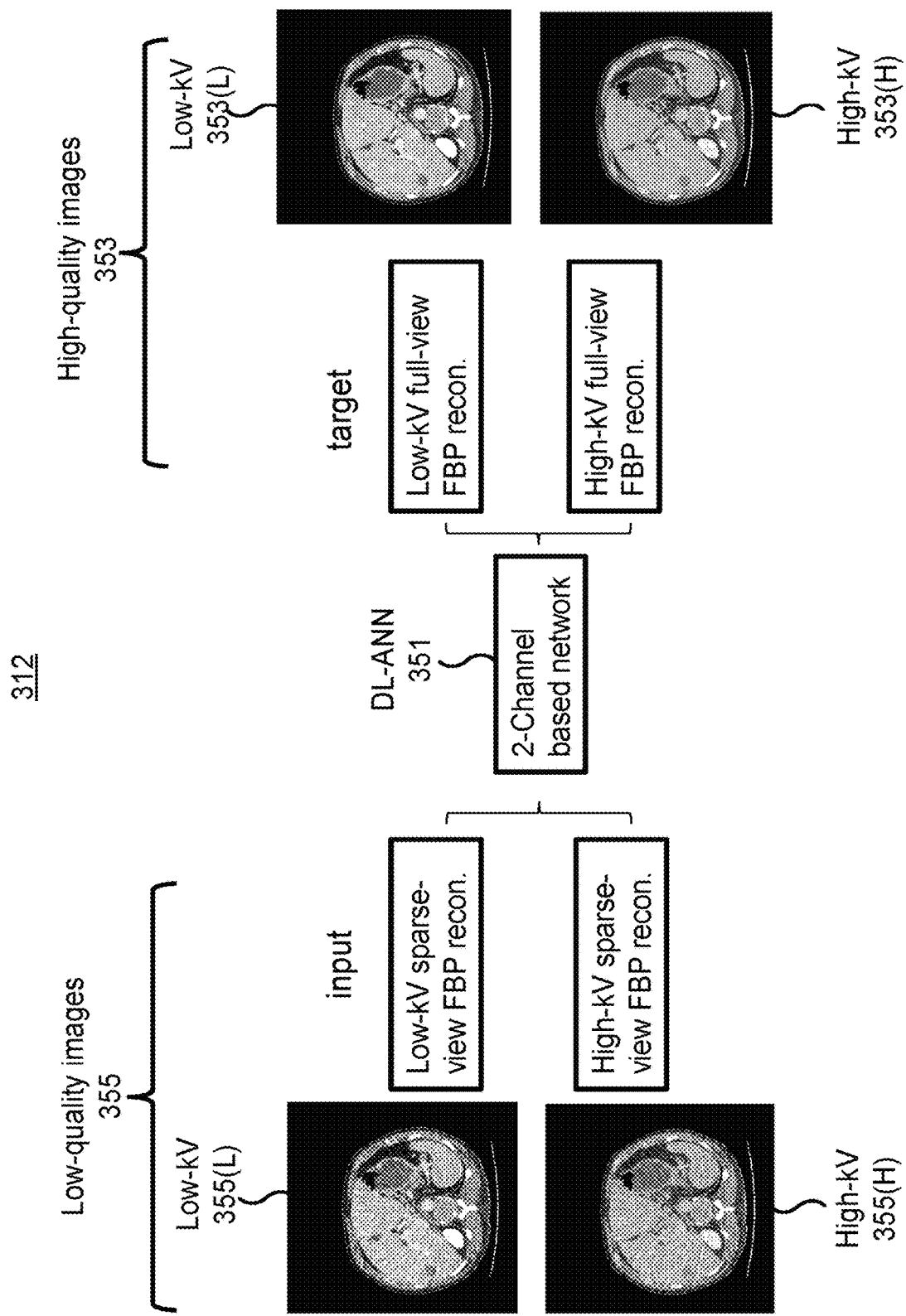
FIG. 8 shows an example of a two-channel DL-ANN network being trained with low- and high-quality image data to correct sparse-view artifacts arising from sparse kVp-switching, according to one implementation.

FIG. 8 shows an example of this, in which the DL-ANN network 351 in trained using two input images (i.e., a low-kV input image 355(L), which is similar to the image in FIG. 5A, and a high-kV input image 355(H), which is similar to the image in FIG. 5B) and two target images (i.e., a low-kV target image 353(L), which is similar to the image in FIG. 7A, and a high-kV target image 353(H), which is similar to the image in FIG. 7B). Further, the DL-ANN network 351 is a two-channel based network that takes two input images 355(L) and 355(H) and generates two results that are compared to the two target images 353(L) and 353(H) via the loss function.

Figure 9:
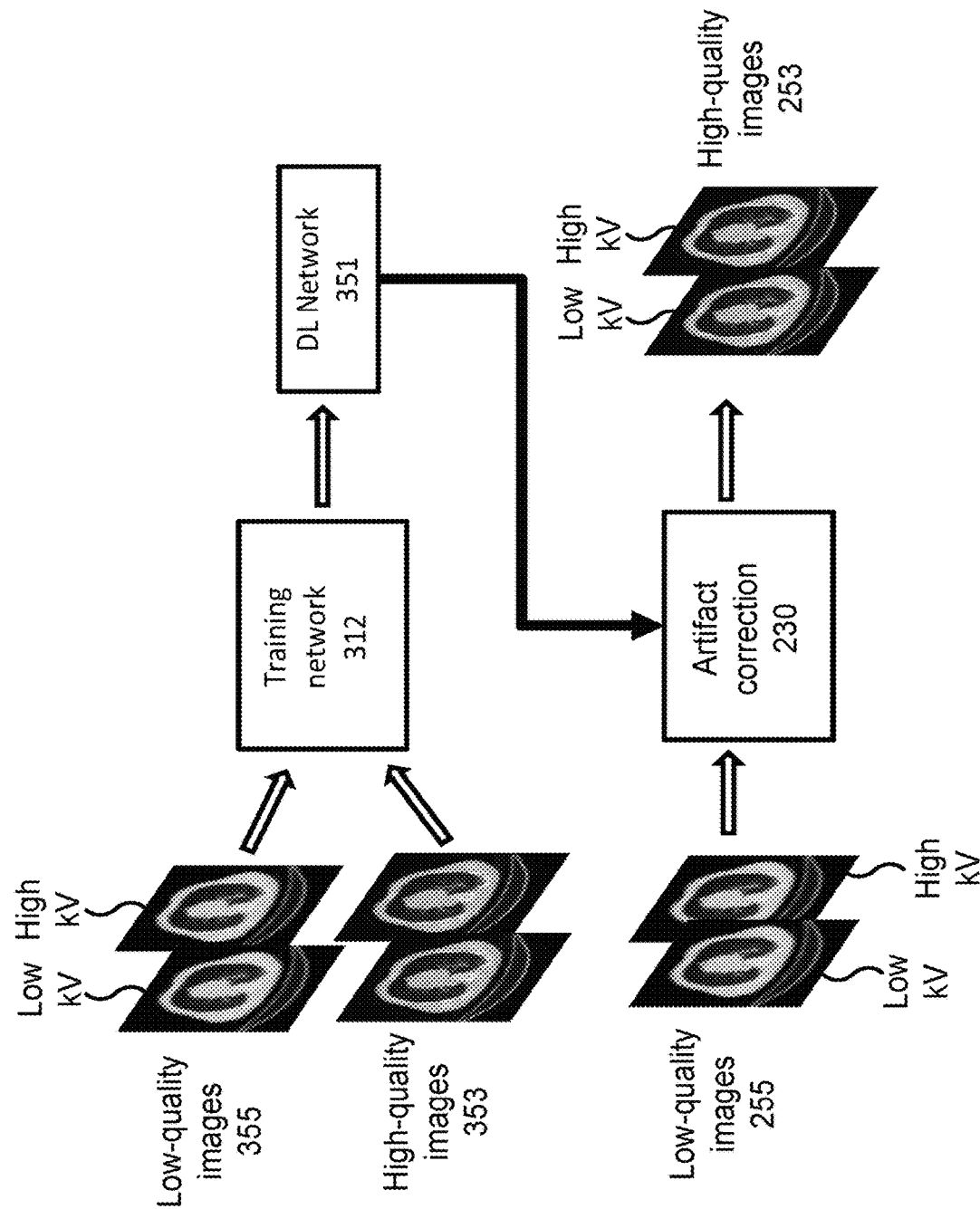
FIG. 9 shows an example of a partial flow diagram for training and using the DL-ANN to correct artifacts arising in images reconstructed from sparse kVp-switching projection data, according to one implementation.

After generating the trained network 351, step 230 of process 202 is used to apply the trained network 351 to generate a high-quality spectral-CT image 253 from the low-quality spectral-CT image 255 arising from step 220 of process 210, as shown in FIG. 9.

Returning to FIG. 6, in process 202, CT projection data 251 that have been generated using sparse kVp-switching are processed using steps 210, 220, 230 and 240 to generate high-quality material images.

In certain implementations, the CT projection data 251 can be projection data acquired from a CT scan that are pre-processed at step 210 (e.g., signal preconditioning, calibration corrections, baseline corrections, beam hardening corrections, etc.). The projection data 251 can be a sinogram that is corrected using various calibration and geometric factors. For example, the pre-processing can include corrections for a detector offset and gain, variations in quantum efficiency in the detectors, etc. Further, these corrections can be based on calibration data, empirical derived parameters, and a priori known parameters.

In step 220 of process 202, the image reconstruction can be performed using a back-projection method, a filtered back-projection method, a Fourier-transform-based image reconstruction method, an iterative image reconstruction method, a matrix-inversion image reconstruction method, a statistical image reconstruction method, or other reconstruction method as would be understood as a person of ordinary skill in the art. For example, the reconstruction method can use a helical reconstruction technique, a cone-beam reconstruction technique, a Feldkamp algorithm, a FBP reconstruction method, and an adaptive iterative dose reduction (AIDR) three-dimensional (3D) reconstruction method with noise reduction in one or both of the image and sinogram domains. The reconstruction can include denoising, corrections to minimize photon starvation in high attenuation regions, corrections to mitigate quantum noise, edge-preservation/enhancement corrections, and filtering (e.g., linear and non-linear filtering and denoising).

In certain implementations, rreconstruction of sparse-view data at each kV respectively results in artifacts due to the missing samples at some view angles. Since low- and high-energy data are complementary to each other, using a two-channel network that analyses the mutual information provides significant benefit over a one-channel network that considers each energy component (kVp setting) separately.

Accordingly, in step 230 of process 202, the network 351 can be a two-channel network that utilizes the complementary information between the low- and high-energy projection data. In certain implementations, the training performed in step 312 uses input images that are generated using the same reconstruction method as in step 220. For example, step 220 can use a FBP based method such as the AIDR 3D method, and the input images in step 312 can be AIDR 3D reconstruction images acquired using sparse kVp-switching with high- and low-kVp values respectively. Since the acquired projection data at each kVp setting is sparse, the resulting image suffers sparse-sampling artifacts. The target images can be the AIDR 3D reconstruction images acquired using projection data from a full-view rotate-rotate dual-energy scan. Since the sampling is complete at each kV for these target images, the target images are artifacts-free. Further the target images can be reconstructed using any other reconstruction method that generates high-quality images with low noise (e.g., an iterative reconstruction method with an edge-preserving or TV regularizer). Thus, in certain implementations of step 230, when the low-quality images 255(H) and 255(L) are applied to the two-channel network 351, the generated high-quality images 253(H) and 253(L) can exhibit both reduced artifact and reduced noise.

Figure 10:
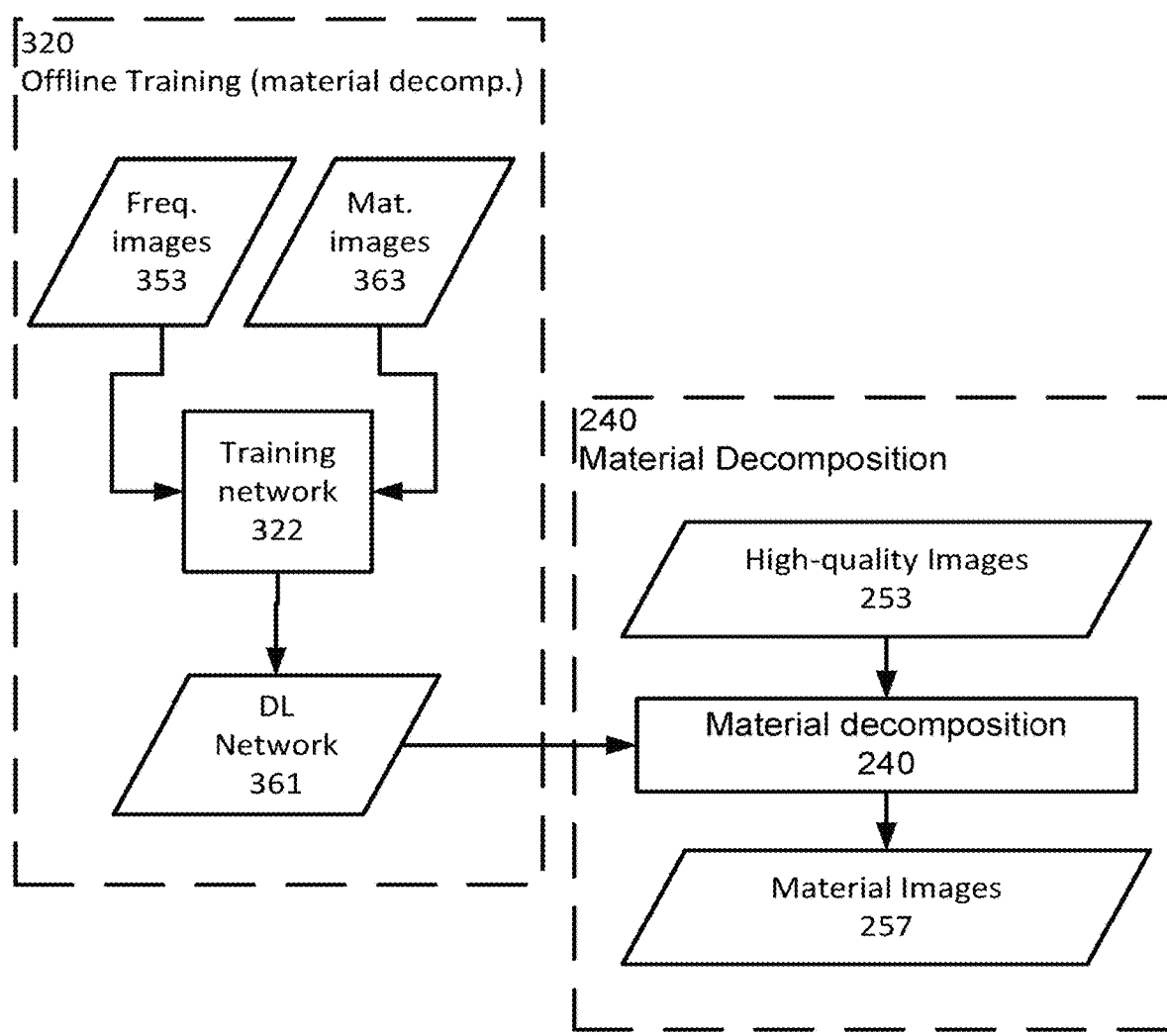
FIG. 10 shows an example of a flow diagram for training and using a DL-ANN to perform image-domain material decomposition, according to one implementation.
Figure 11:
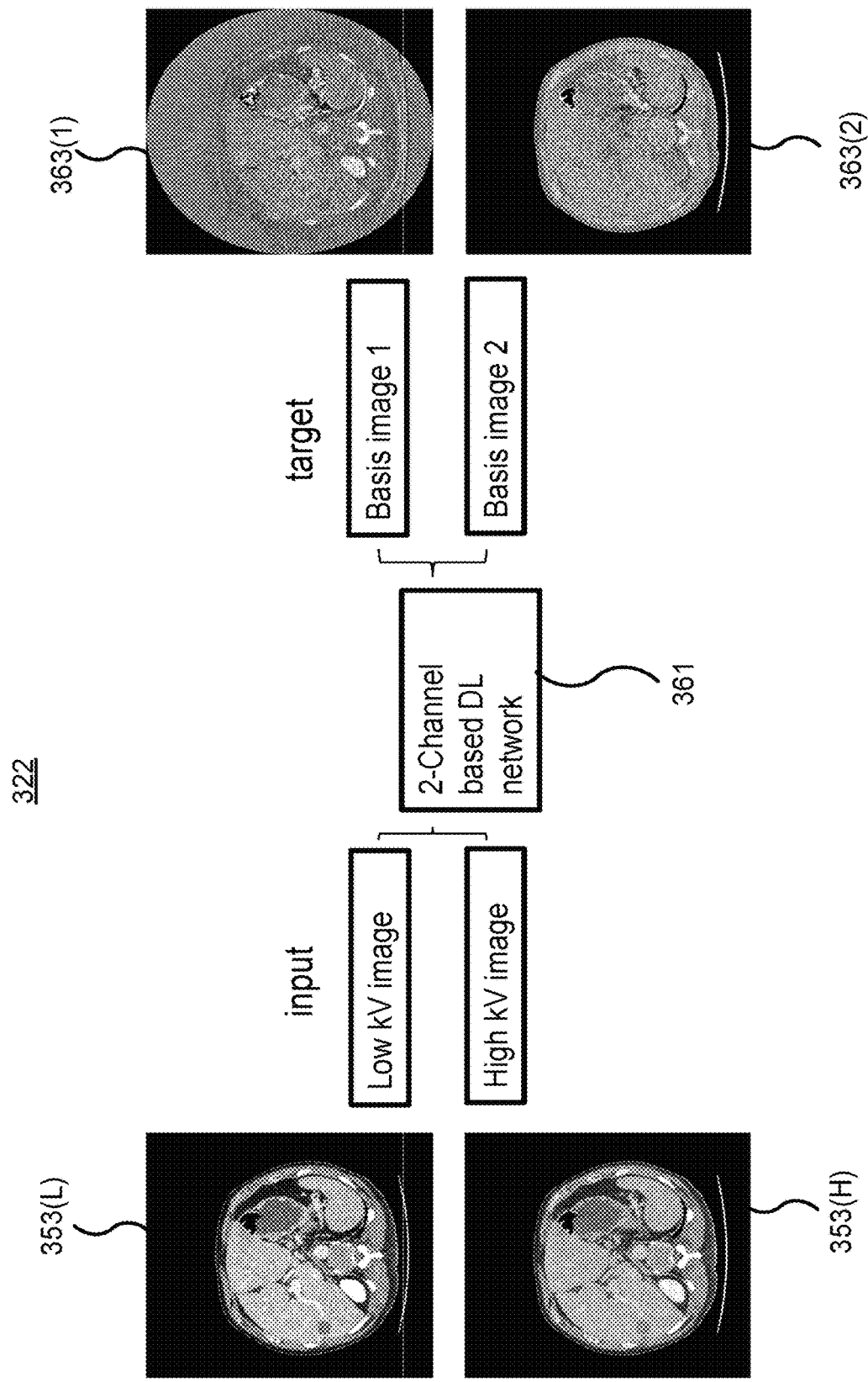
FIG. 11 shows an example of a two-channel DL-ANN network being trained to perform the image-domain material decomposition, according to one implementation.
Figure 12:
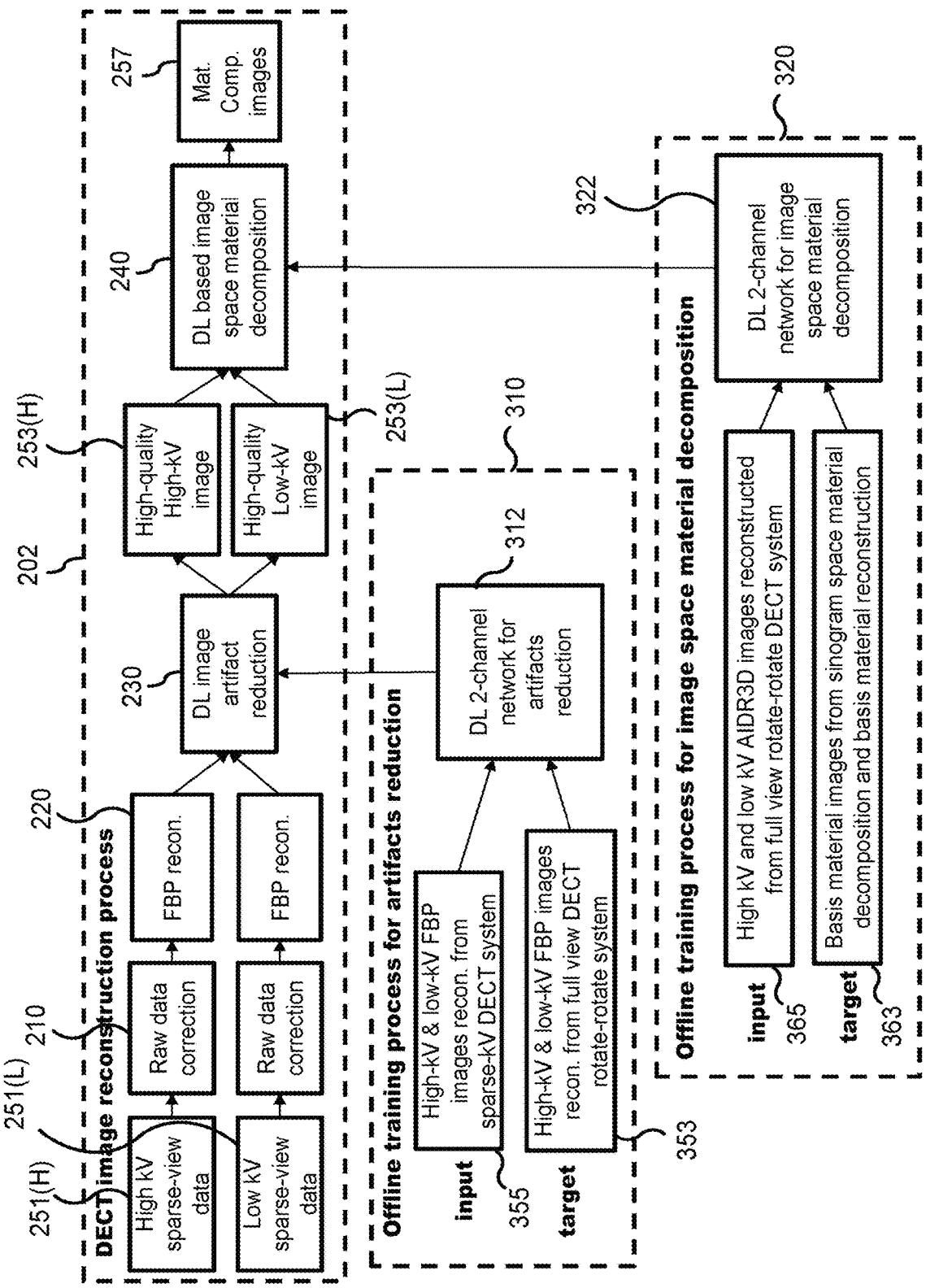
FIG. 12 shows a flow diagram in which two separate DL-ANN networks are respectively trained and used to correct artifacts and perform image-domain material decomposition, according to one implementation.

In step 240 of process 202, material decomposition can be performed on the images 253(H) and 253(L) to generate material-component images 257. In general, any material decomposition method can be used to generate material-component images 257. FIGS. 10-12 show an implementation of method 200 in which step 240 is performed using a DL-ANN network 361 to perform the material decomposition.

As discussed above, in general, the material decomposition mapping from the spectral domain to the material-component domain can be performed either before or after the image reconstruction process. However, in sparse kVp-switching material decomposition is simpler to perform in the image domain than in the projection (sinogram) domain. As discussed above, to perform material decomposition in the projection (sinogram) domain, the projection data should include identical (or nearly identical) X-ray trajectories for each of the measured energy components. In fast kVp-switching, this achieved because the CT scanner has rotated very little between adjacent high-kV and low-kV. However, for sparse kVp-switching the differences can become large between the projection angles for high- and low-kV and low-kVp settings, making projection-domain material decomposition challenging.

The DL-ANN network 361 can be particular effective at addressing the challenges of image-domain material decomposition in dual-energy CT (DECT). There are two challenges for conventional image-space decomposition. First, the X-ray spectrum of the X-ray beam can be spatially varying due to bowtie filtration. Therefore, the image-space material decomposition matrix is ideally also spatially varying. Second, correcting for beam-hardening artifacts is straightforward and efficient in sinogram-domain material decomposition because the contributions of each material are known along the X-ray trajectories. In contrast, for image-space material decomposition, the beam-hardening correction is more complicated and typically less efficient, requiring time consuming, iterative corrections. Using the DL method described herein, however, image-space material decomposition with beam-hardening corrections can be performed more efficiently than in previous methods. For example, to address the above challenges, deep learning is used with a two-channel network 361 to quickly perform material decomposition while correcting for beam hardening and for spatial variations in the spectrum of the X-ray beam.

To realize these improvements, FIGS. 10 and 11 shows that the training data includes that the input images are the two high-quality kVp images 353(H) and 353(L), and that the target images are a basis-material image for a first material component 363(1) and a basis-material image for a second material component 363(2). The material-component images 363(1) and 363(2) can be obtained by performing sinogram-domain material decomposition on full-scan projection data and then reconstructing high-quality material images 363(1) and 363(2) from material component projection data (i.e., material decomposition is performed in the sinogram domain prior to reconstruction). Thus, the material-component images 363(1) and 363(2) due not suffer from inaccurate beam-hardening corrections and spatial-spectrum corrections for the X-ray beam because spatially variations in the spectrum and beam hardening corrections can be fully modeled in the sinogram domain. Accordingly, by training on the material-component images 363(1) and 363(2), the DL-ANN network 361 can be trained to more accurately and efficiently perform image-domain material decomposition than is achieved in related image-domain methods.

In FIG. 12, a flow diagram of method 200 is provided of an implementation that includes both the artifact reduction DL-ANN network 351 and the image-domain material decomposition DL-ANN network 361.

Figure 13:
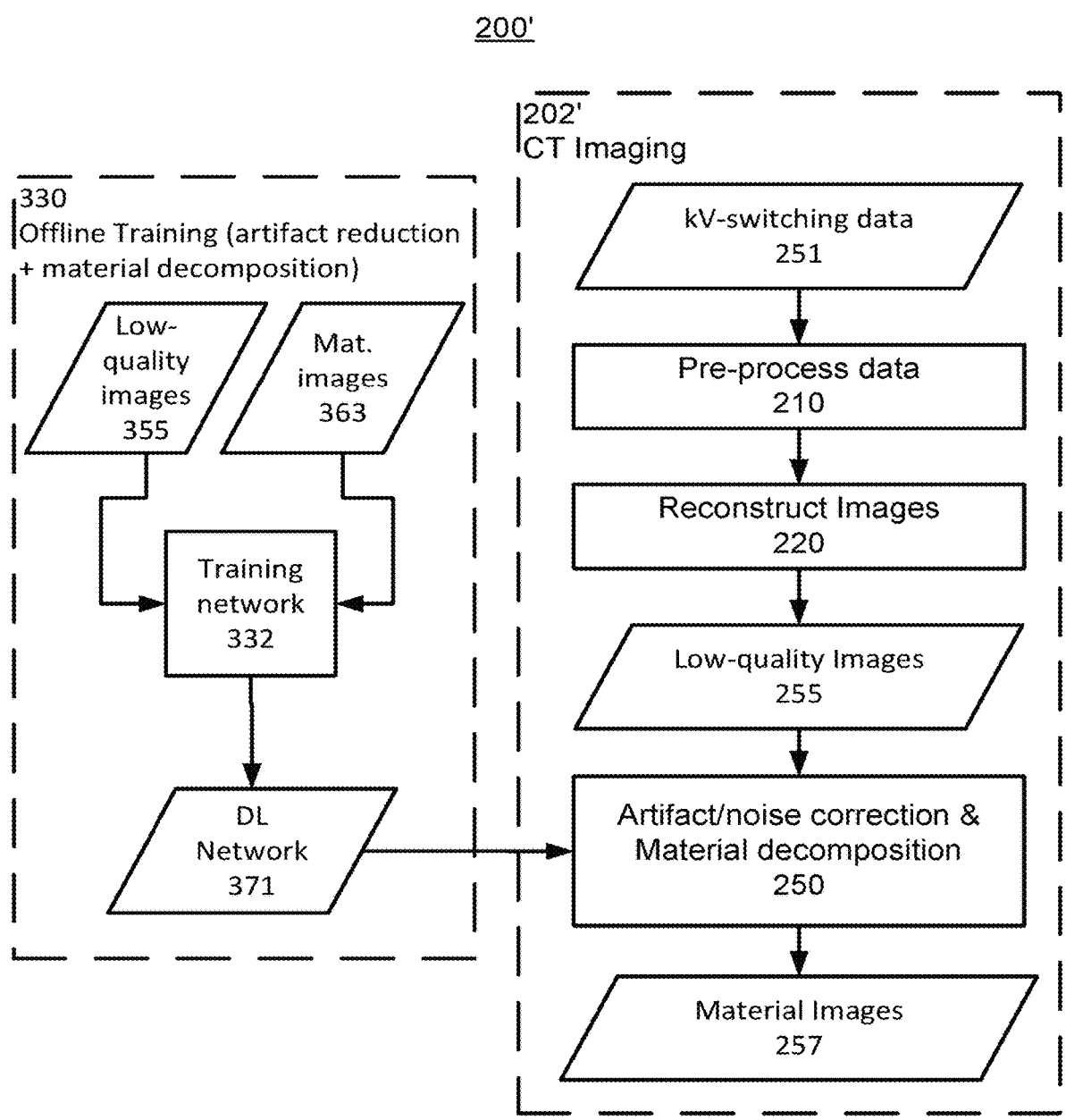
FIG. 13 shows a flow diagram in which a single two-channel DL-ANN network is trained and used to correct artifacts and perform image-domain material decomposition as an integrated process, according to one implementation.
Figure 14:
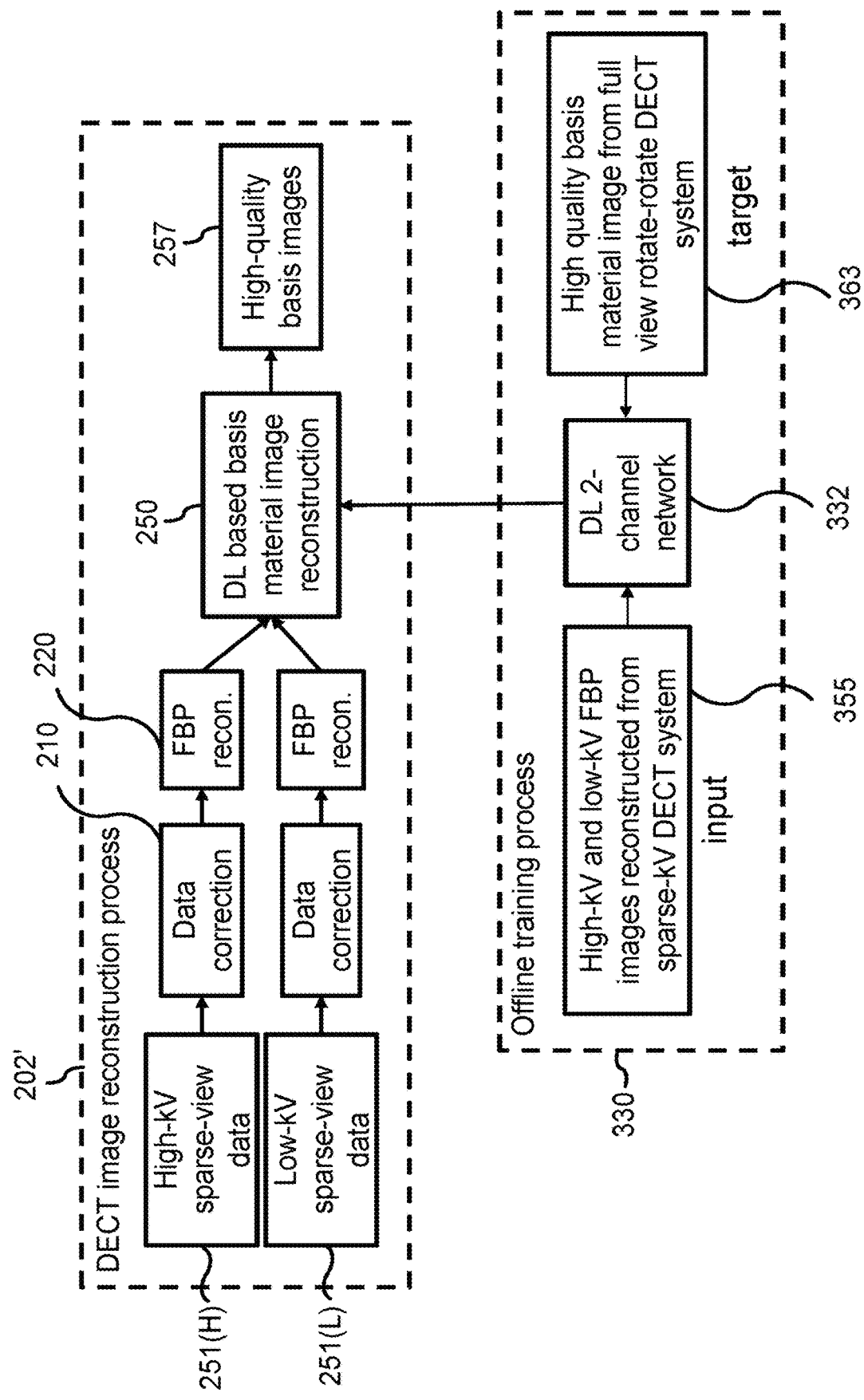
FIG. 14 shows another flow diagram in which the single two-channel DL-ANN network is trained and used to correct artifacts and perform image-domain material decomposition as an integrated process, according to one implementation.
Figure 15:
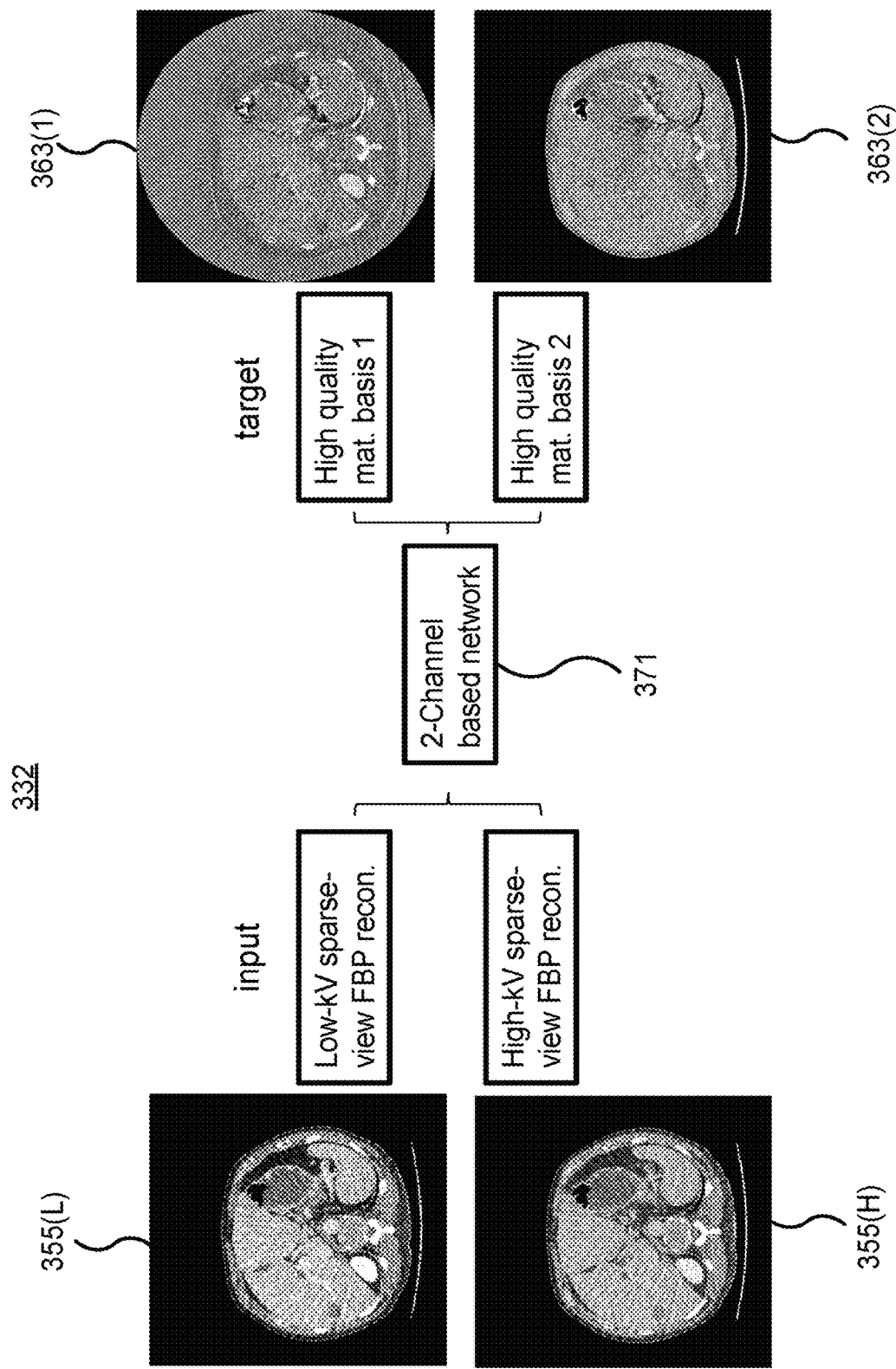
FIG. 15 shows the single two-channel DL-ANN network being trained to both correct artifacts and perform image-domain material decomposition as an integrated process, according to one implementation.

FIGS. 13 and 14 shows flow diagrams of method 200', which is a variation of method 200 in which the artifact reduction and material decomposition of step 230 and 240 have been combined into a single step 250. The DL-ANN network 371 combines both functions of artifact reduction and material decomposition, which are integrated into a single network because, as shown in FIG. 15. The DL-ANN network 371 is trained in step 332 using the low-quality images 355(H) and 355(L) as inputs and the high-quality material images 363(1) and 363(2) as targets.

Figure 16:
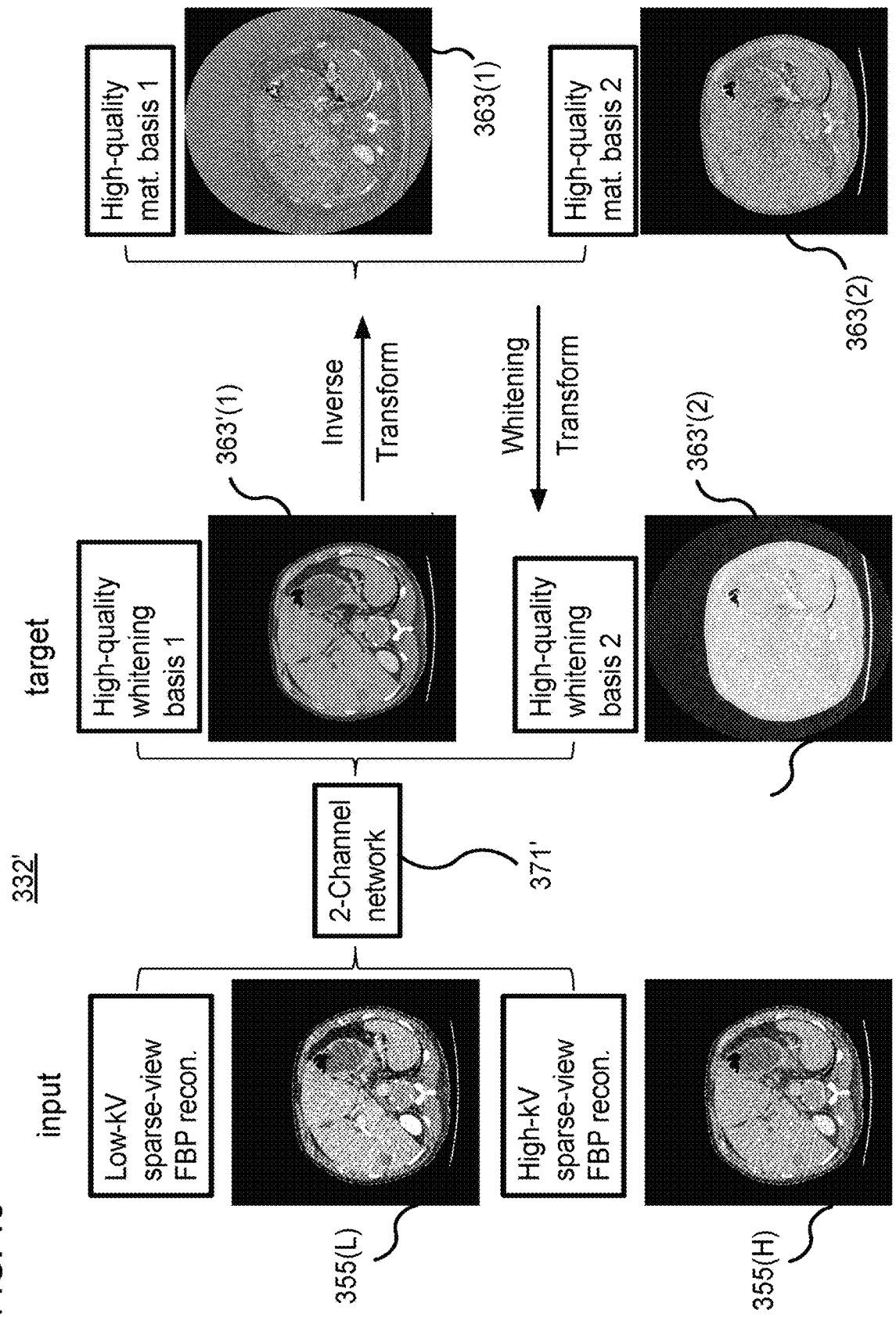
FIG. 16 shows the single two-channel DL-ANN network being trained in the whitening transform domain to both correct artifacts and perform image-domain material decomposition as an integrated process, according to one implementation.

In certain implementations, in training step 332, the input images to the DL-ANN network 371 are the high- and low-kVp images that have been reconstructed using, e.g., an AIDR 3D or a FBP reconstruction method. Since the images are reconstructed from incomplete sampling data, the input images are subject to sparse-sampling artifacts. The target images of the DL-ANN network 371 are the high-quality basis-material images from a full-view rotate-rotate dual-energy CT scan, as shown in FIG. 15. The DL-ANN network 371 can use a two-channel DL-ANN network structure FIG. 16 shows a diagram of a step 332', which is a variation of step 332'. In step 332", the target images are whitening-transformed images 363'(1) and 363'(2) generated by performing a whitening transform on the high-quality material images 363(1) and 363(2). That is, the material-component images 363(1) and 363(2) are related to the whitening-transformed images 363'(1) and 363'(2) by a whitening transform that de-correlates noise. Thus, when the network 371' is applied to the low-quality images 255 in step 250 of process 202', the result will be whitening-transformed images 257'(1) and 257'(2), and, in step 250, an inverse whitening is performed on the whitening-transformed images 257'(1) and 257'(2) to generate the material-component images 257(1) and 257(2).

To optimize the mono-energetic image quality at clinically relevant diagnostic energy range, whitening transform can be applied to the deep learning target image. When the whitening transform matrix is estimated from the 75 keV linear attenuate coefficients, the deep learning tends to optimize the network coefficients to provide high-quality 75 keV mono-energetic image. The basis material decomposition can introduce correlated noise to the basis material image. The whitening transform can de-correlate the noise in two basis material images. Therefore, the trained network can efficiently reduce noise in learning process. In reconstruction process 202, the high-quality material-basis images 257(1) and 257(2) can be obtained by performing an inverse whitening transformation on the output images 257'(1) and 257'(2) from the DL-ANN network 371', when applied in step 250.

Figure 17:
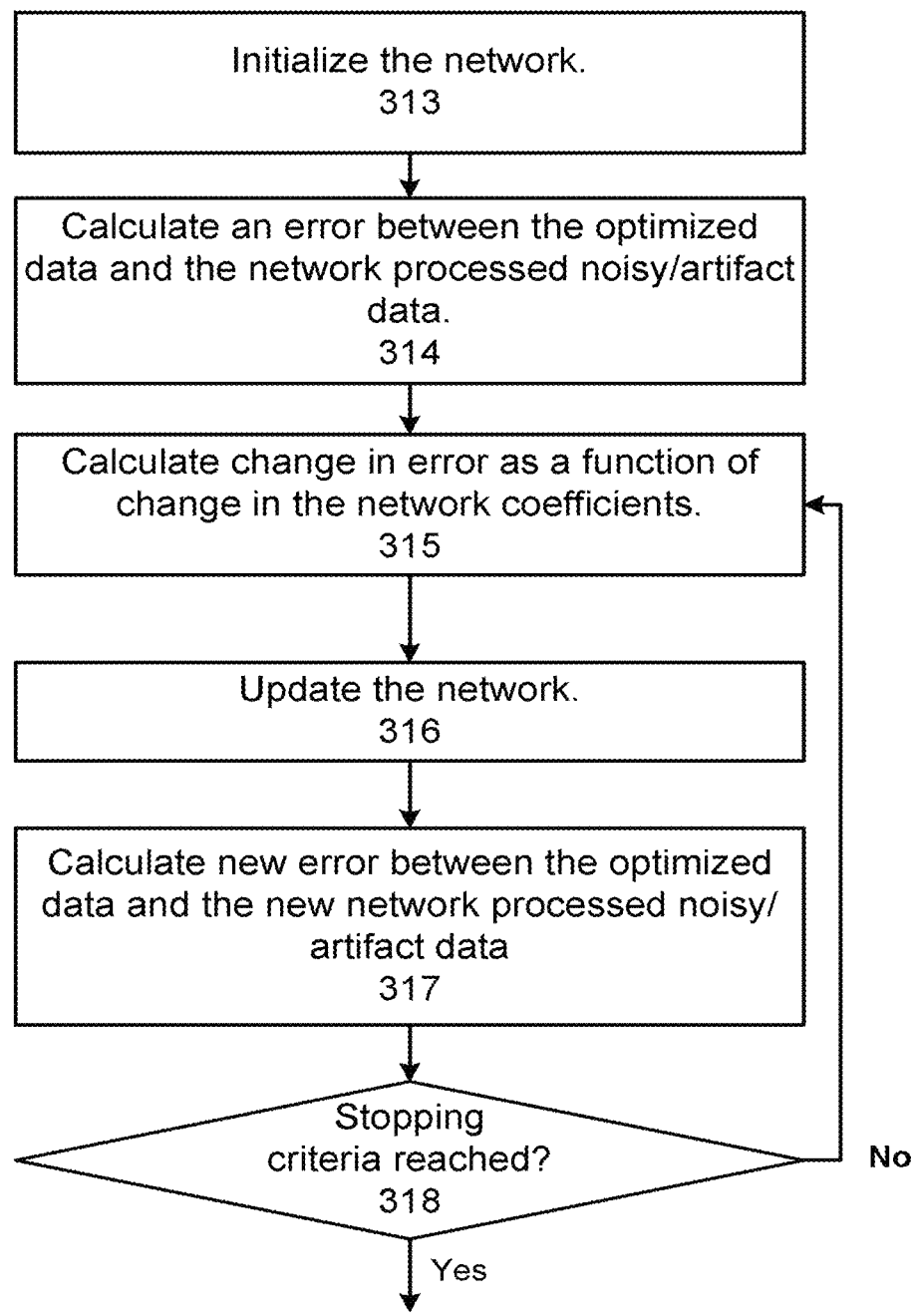
FIG. 17 shows a flow diagram for iteratively adjusting coefficients of a DL-ANN network to optimize a loss-error function, and thereby training the DL-ANN, according to one implementation.

Now a more detailed description of training a DL-ANN network is provided. This description is illustrated using step 312 as an example of training a network, but also applies to the training in performed steps 322, 332, and 332', as would be understood by a person of ordinary skill in the art. FIG. 17 shows a flow diagram of one implementation of the training step 312. In step 312, low-quality (e.g., noisy) images 355 and high-quality (e.g., optimized) images 353 are used as training data to train a DL-ANN network, resulting in the DL-ANN network being output from step 318. In general, the images 355 can be any defect-exhibiting images or input images, for which the "defect" can be any undesirable characteristic that can be affected through image processing (e.g., noise or an artifact). Similarly, images 353 can be referred to as target data, defect-reduced data, defect-minimized data, or optimized data, for which the "defect" is less than in the images 355. The offline DL training step 312 trains the DL-ANN network 351 using a large number of input images 355 that are paired with corresponding target images 353 to train the DL-ANN network 351 to produce images resembling the target images 353 from the input images 355.

In step 312, a set of training data is obtained, and the network 351 is iteratively updated to reduce the error (e.g., the value produced by a loss function). In other words, DL-ANN network infers the mapping implied by the training data, and the cost function produces an error value related to the mismatch between the target images 353 and the result produced by applying a current incarnation of the DL-ANN network 351 to the input images 355. For example, in certain implementations, the cost function can use the mean-squared error to minimize the average squared error. In the case of a of multilayer perceptrons (MLP) neural network, the backpropagation algorithm can be used for training the network by minimizing the mean-squared-error-based cost function using a (stochastic) gradient descent method.

In step 313 of step 312, an initial guess is generated for the coefficients of the DL-ANN network 351. For example, the initial guess can be based on a priori knowledge of the region being imaged or one or more exemplary denoising methods, edge-detection methods, and/or blob detection methods. Additionally, the initial guess can be based on one of a LeCun initialization, an Xavier initialization, and a Kaiming initialization.

Steps 314 through 318 provide a non-limiting example of an optimization method for training the DL-ANN network 351.

In step 314, an error is calculated (e.g., using a loss function or a cost function) to represent a measure of the difference (e.g., a distance measure) between the target images 353 (i.e., ground truth) and input images 355 after applying a current version of the network 351. The error can be calculated using any known cost function or distance measure between the image data, including those cost functions described above. Further, in certain implementations the error/loss function can be calculated using one or more of a hinge loss and a cross-entropy loss.

Additionally, the loss function can be combined with a regularization approach to avoid overfitting the network to the particular instances represented in the training data. Regularization can help to prevent overfitting in machine learning problems. If trained too long, and assuming the model has enough representational power, the network will learn the noise specific to that dataset, which is referred to as overfitting. In case of overfitting, the DL-ANN becomes a poor generalization, and the variance will be large because the noise varies between datasets. The minimum total error occurs when the sum of bias and variance are minimal. Accordingly, it is desirable to reach a local minimum that explains the data in the simplest possible way to maximize the likelihood that the trained network represents a general solution, rather than a solution particular to the noise in the training data. This goal can be achieved, e.g., by early stopping, weight regularization, lasso regularization, ridge regularization, or elastic net regularization.

In certain implementations, the network 351 is trained using backpropagation. Backpropagation can be used for training neural networks and is used in conjunction with gradient descent optimization methods. During a forward pass, the algorithm computes the network's predictions based on the current parameters Θ. These predictions are then input into the loss function, by which they are compared to the corresponding ground truth labels (i.e., the high-quality image 353). During the backward pass, the model computes the gradient of the loss function with respect to the current parameters, after which the parameters are updated by taking a step of size of a predefined size in the direction of minimized loss (e.g., in accelerated methods, such that the Nesterov momentum method and various adaptive methods, the step size can be selected to more quickly converge to optimize the loss function).

The optimization method by which the back projection is performed can use one or more of gradient descent, batch gradient descent, stochastic gradient descent, and mini-batch stochastic gradient descent. Additionally, the optimization method can be accelerated using one or more momentum update techniques in the optimization approach that results in faster convergence rates of stochastic gradient descent in deep networks, including, e.g, Nesterov momentum technique or an adaptive method, such as Adagrad sub-gradient method, an Adadelta or RMSProp parameter update variation of the Adagrad method, and an Adam adaptive optimization technique. The optimization method can also apply a second order method by incorporating the Jacobian matrix into the update step.

The forward and backwards passes can be performed incrementally through the respective layers of the network. In the forward pass, the execution starts by feeding the inputs through the first layer, thus creating the output activations for the subsequent layer. This process is repeated until the loss function at the last layer is reached. During the backward pass, the last layer computes the gradients with respect to its own learnable parameters (if any) and also with respect to its own input, which serves as the upstream derivatives for the previous layer. This process is repeated until the input layer is reached.

Returning to the non-limiting example shown in FIG. 17, step 315 determines a change in the error as a function of the change in the network can be calculated (e.g., an error gradient), and this change in the error can be used to select a direction and step size for a subsequent change to the weights/coefficients of the DL-ANN network 351. Calculating the gradient of the error in this manner is consistent with certain implementations of a gradient descent optimization method. In certain other implementations, this step can be omitted and/or substituted with another step in accordance with another optimization algorithm (e.g., a non-gradient descent optimization algorithm like simulated annealing or a genetic algorithm), as would be understood by one of ordinary skill in the art.

In step 316, a new set of coefficients are determined for the DL-ANN network 351. For example, the weights/coefficients can be updated using the changed calculated in step 315, as in a gradient descent optimization method or an over-relaxation acceleration method.

In step 317, a new error value is calculated using the updated weights/coefficients of the DL-ANN network 351.

In step 318, predefined stopping criteria are used to determine whether the training of the network is complete. For example, the predefined stopping criteria can evaluate whether the new error and/or the total number of iterations performed exceed predefined values. For example, the stopping criteria can be satisfied if either the new error falls below a predefined threshold or if a maximum number of iterations is reached. When the stopping criteria is not satisfied the training process performed in step 312 will continue back to the start of the iterative loop by returning and repeating step 315 using the new weights and coefficients (the iterative loop includes steps 315, 316, 317, and 318). When the stopping criteria are satisfied the training process performed in step 312 is completed.

Figure 18A:
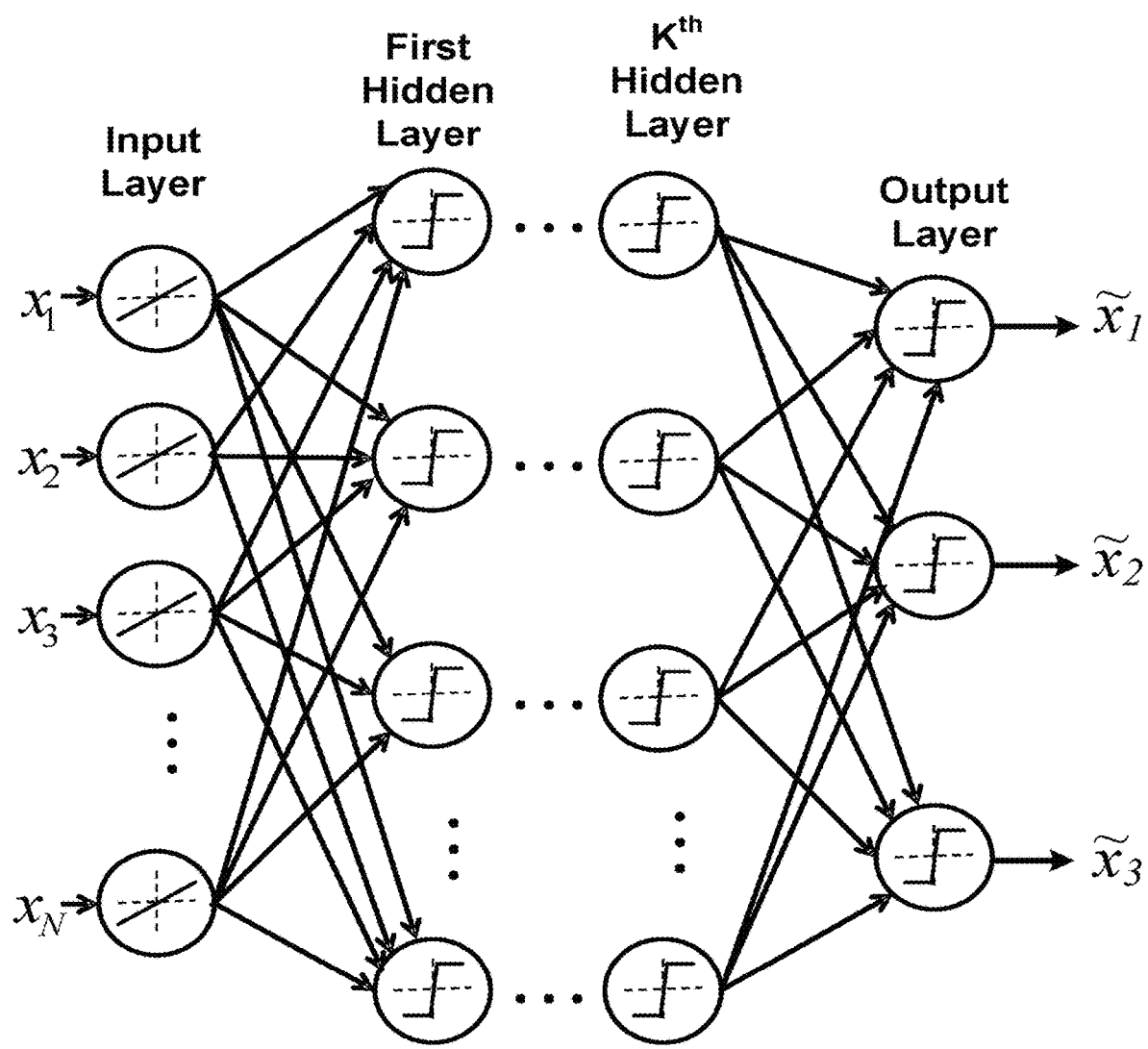
FIG. 18A shows an example of a feedforward ANN, according to one implementation.
Figure 18B:
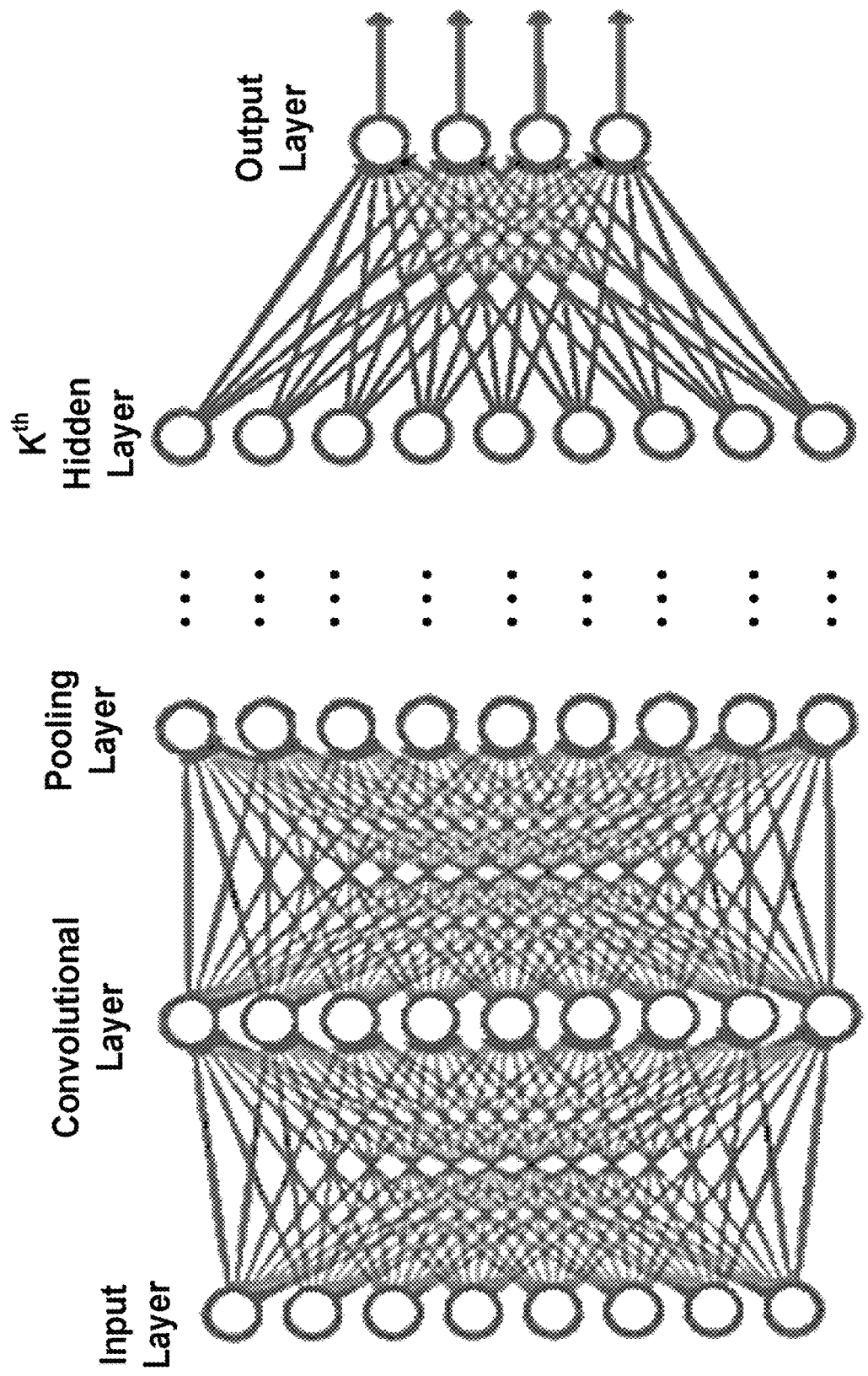
FIG. 18B shows an example of a type of ANN referred to as a convolutional neural network (CNN), according to one implementation.

FIGS. 18A and 18B show various examples of the interconnections between layers in the DL-ANN network 351. The DL-ANN network 351 can include fully connected, convolutional, and the pooling layer, all of which are explained below. In certain preferred implementations of the DL-ANN network 351, convolutional layers are placed close to the input layer, whereas fully connected layers, which perform the high-level reasoning, are place further down the architecture towards the loss function. Pooling layers can be inserted after convolutions and proved a reduction lowering the spatial extent of the filters, and thus the amount of learnable parameters. Activation functions are also incorporated into various layers to introduce nonlinearity and enable the network to learn complex predictive relationships. The activation function can be a saturating activation functions (e.g., a sigmoid or hyperbolic tangent activation function) or rectified activation function (e.g., the Rectified Linear Unit (ReLU) applied in the first and second examples discussed above). The layers of the DL-ANN network 351 can also incorporate batch normalization, as also exemplified in the first and second examples discussed above.

FIG. 18A shows an example of a general artificial neural network (ANN) having N inputs, K hidden layers, and three outputs. Each layer is made up of nodes (also called neurons), and each node performs a weighted sum of the inputs and compares the result of the weighted sum to a threshold to generate an output. ANNs make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The simplest ANN has three layers, and is called an autoencoder. The DL-ANN network 351 can have more than three layers of neurons, and has as many outputs neurons as input neurons, wherein N is the number of pixels in the reconstructed image. The synapses (i.e., the connections between neurons) store values called "weights" (also interchangeably referred to as "coefficients" or "weighting coefficients") that manipulate the data in the calculations. The outputs of the ANN depend on three types of parameters: (i) the interconnection pattern between the different layers of neurons, (ii) the learning process for updating the weights of the interconnections, and (iii) the activation function that converts a neuron's weighted input to its output activation.

Mathematically, a neuron's network function m (x) is defined as a composition of other functions $n_i(x)$, which can further be defined as a composition of other functions. This can be conveniently represented as a network structure, with arrows depicting the dependencies between variables, as shown in FIG. 18. For example, the ANN can use a nonlinear weighted sum, wherein $m(x)=K(\Sigma_i w_i n_i(x))$, where K (commonly referred to as the activation function) is some predefined function, such as the hyperbolic tangent.

In FIG. 18A (and similarly in FIG. 18B), the neurons (i.e., nodes) are depicted by circles around a threshold function. For the non-limiting example shown in FIG. 18A, the inputs are depicted as circles around a linear function, and the arrows indicate directed connections between neurons. In certain implementations, the DL-ANN network 351 is a feedforward network.

FIG. 18B shows a non-limiting example in which the DL-ANN network 351 is a convolutional neural network (CNN). CNNs are type of ANN that has beneficial properties for image processing, and, therefore, have specially relevancy for the applications of image denoising. CNNs use feed-forward ANNs in which the connectivity pattern between neurons can represent convolutions in image processing. For example, CNNs can be used for image-processing optimization by using multiple layers of small neuron collections which process portions of the input image, called receptive fields. The outputs of these collections can then tiled so that they overlap, to obtain a better representation of the original image. This processing pattern can be repeated over multiple layers having alternating convolution and pooling layers.

Following after a convolutional layer, a CNN can include local and/or global pooling layers, which combine the outputs of neuron clusters in the convolution layers. Additionally, in certain implementations, the CNN can also include various combinations of convolutional and fully connected layers, with pointwise nonlinearity applied at the end of or after each layer.

CNNs have several advantages for image processing. To reduce the number of free parameters and improve generalization, a convolution operation on small regions of input is introduced. One significant advantage of certain implementations of CNNs is the use of shared weight in convolutional layers, which means that the same filter (weights bank) is used as the coefficients for each pixel in the layer; this both reduces memory footprint and improves performance. Compared to other image-processing methods, CNNs advantageously use relatively little pre-processing. This means that the network is responsible for learning the filters that in traditional algorithms were hand-engineered. The lack of dependence on prior knowledge and human effort in designing features is a major advantage for CNNs.

Figure 19A:
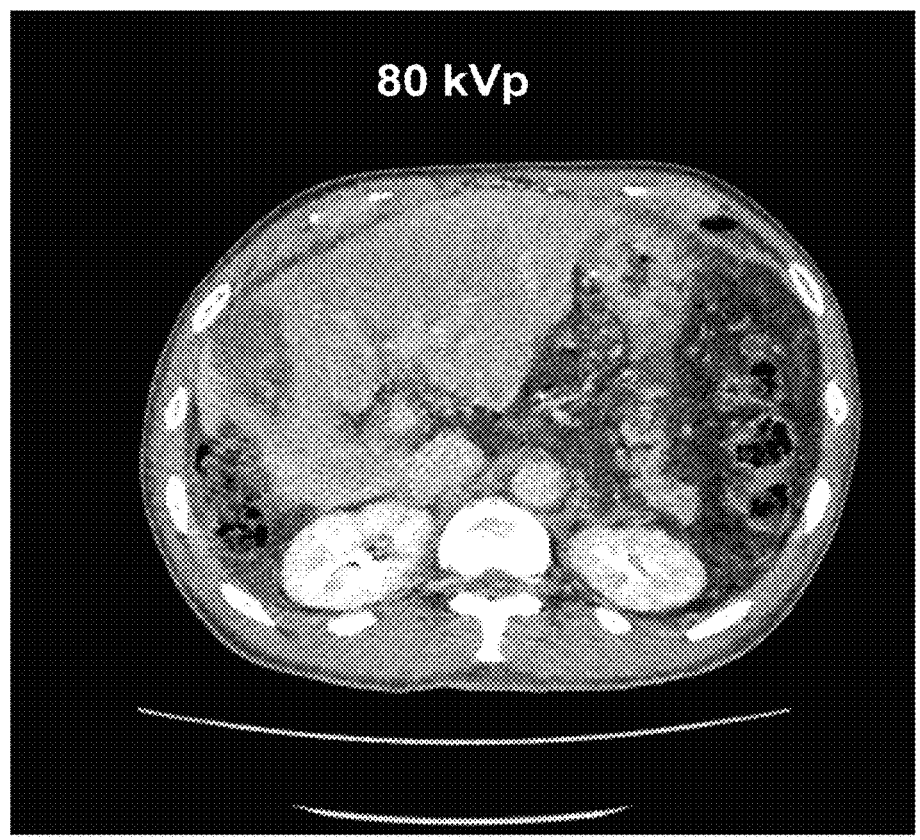
FIG. 19A shows an example of the 80 kVp image in FIG. 5A after it has been applied to the artifact-reducing DL-ANN at step 230 of method 202, according to one implementation.
Figure 19B:
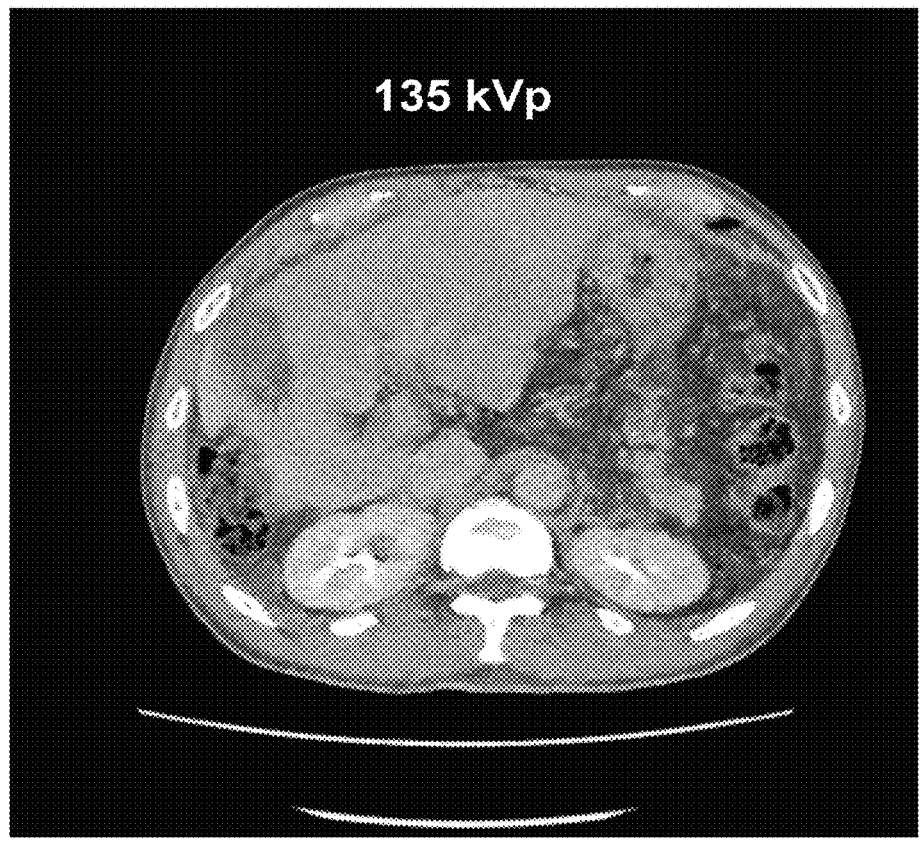
FIG. 19B shows an example of the 135 kVp image in FIG. 5B after it has been applied to the artifact-reducing DL-ANN at step 230 of method 202), according to one implementation.

FIGS. 19A and 19B respectively show examples of high-quality low- and high-kVp images generated by step 230 from the low-quality low- and high-kVp images in FIGS. 5A and 5B. As can be seen by comparing the low- and high-quality images, processing using the network 351 produces a significant improvement in image quality.

Figure 20A:
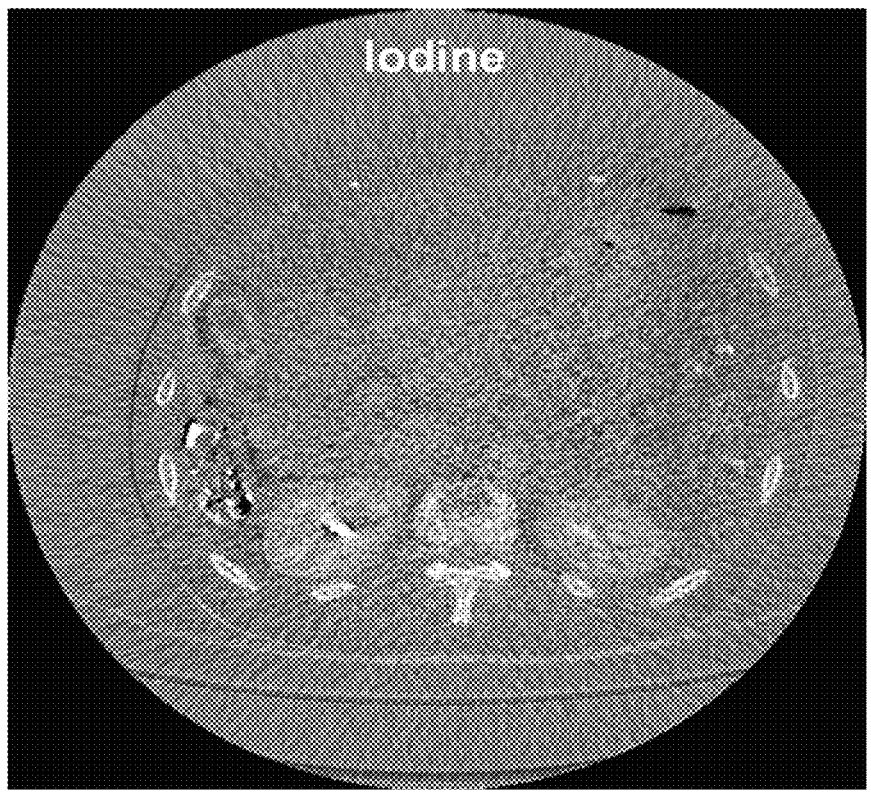
FIG. 20A shows an example of an image for an iodine material component generated without using artifact reducing and material decomposition DL-ANN networks, according to one implementation.
Figure 20B:
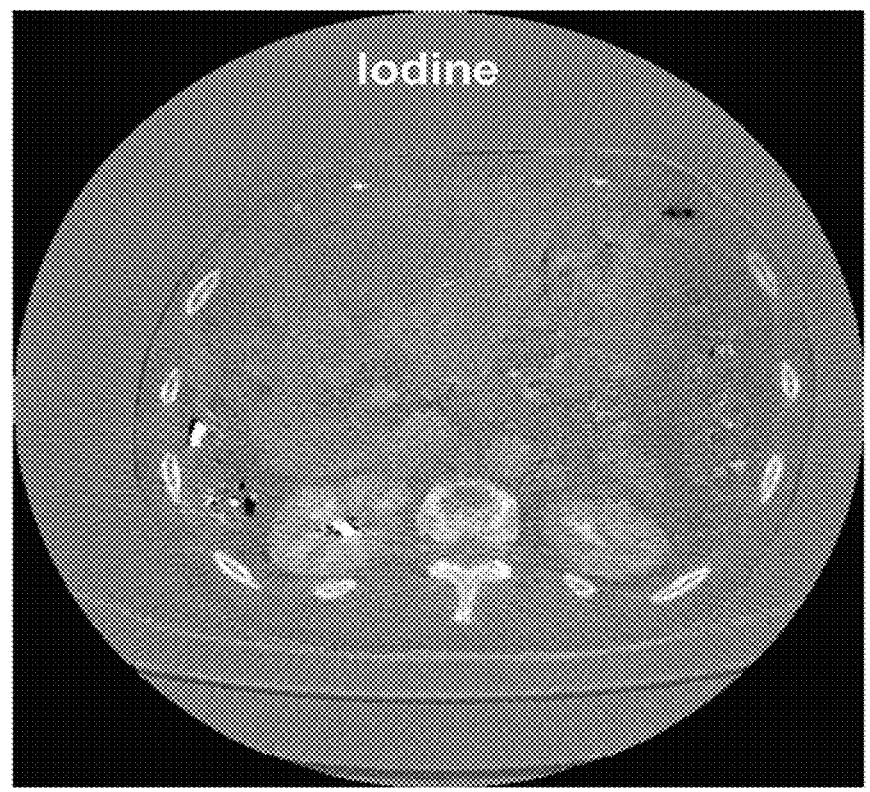
FIG. 20B shows an example of an image for the iodine material component generated using the artifact reducing and material decomposition DL-ANN networks, according to one implementation.
Figure 20C:
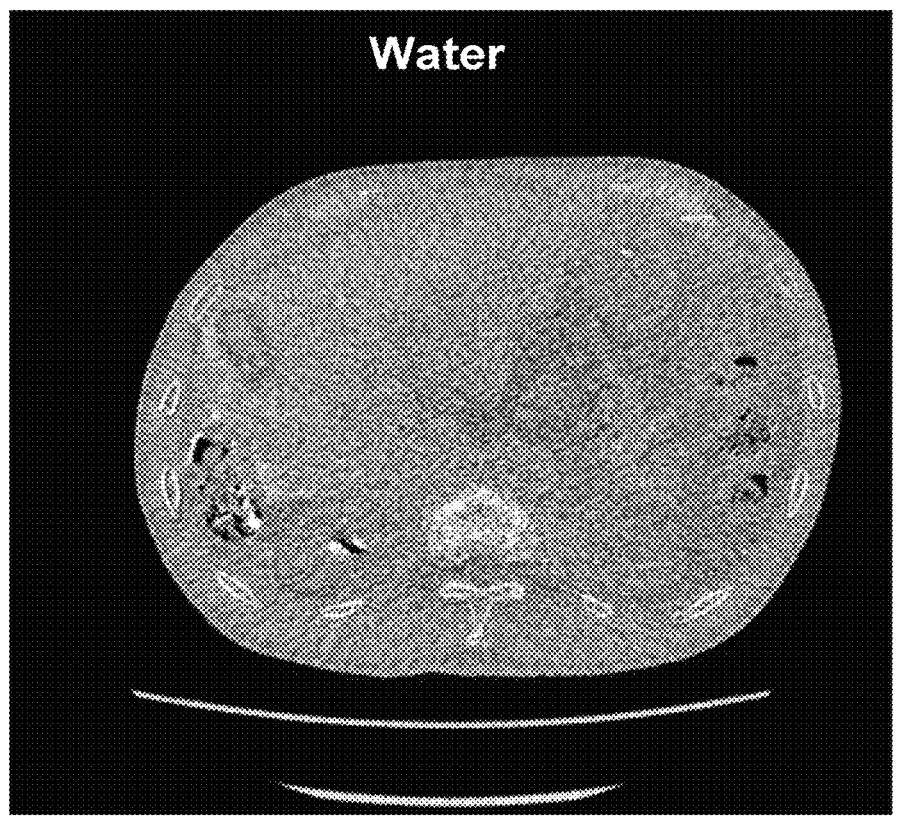
FIG. 20C shows an example of an image for a water material component generated without using the artifact reducing and material decomposition DL-ANN networks, according to one implementation.
Figure 20D:
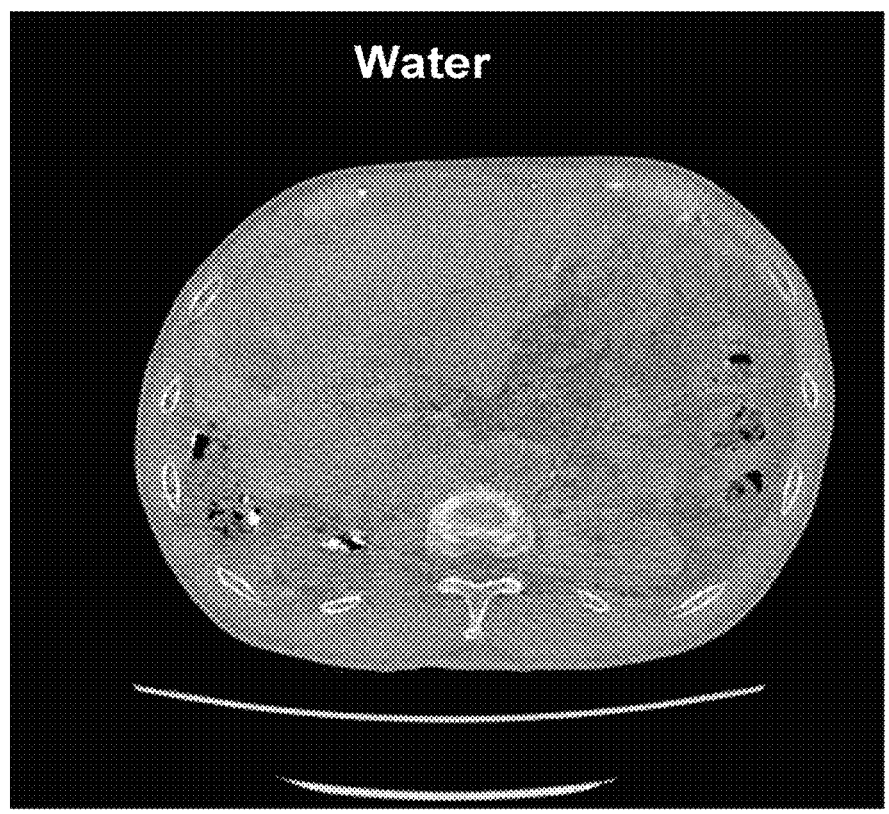
FIG. 20D shows an example of an image for the water material component generated using the artifact reducing and material decomposition DL-ANN networks, according to one implementation.

FIGS. 20A and 20C respectively show iodine and water material component images generated using conventional material decomposition methods on the low-quality low- and high-kVp images in FIGS. 5A and 5B. FIGS. 20B and 20D respectively show iodine and water material component images generated using applying the high-quality images in FIGS. 19A and 19B to the DL-ANN network 361 in step 240. A comparison of the iodine images in FIGS. 20A and 20B (and similarly a comparison of the water images in FIGS. 20C and 20D) reveals that method 200 produces a significant improvement in image quality for images reconstructed from sparse kVp-switching projection data.

Figure 21:
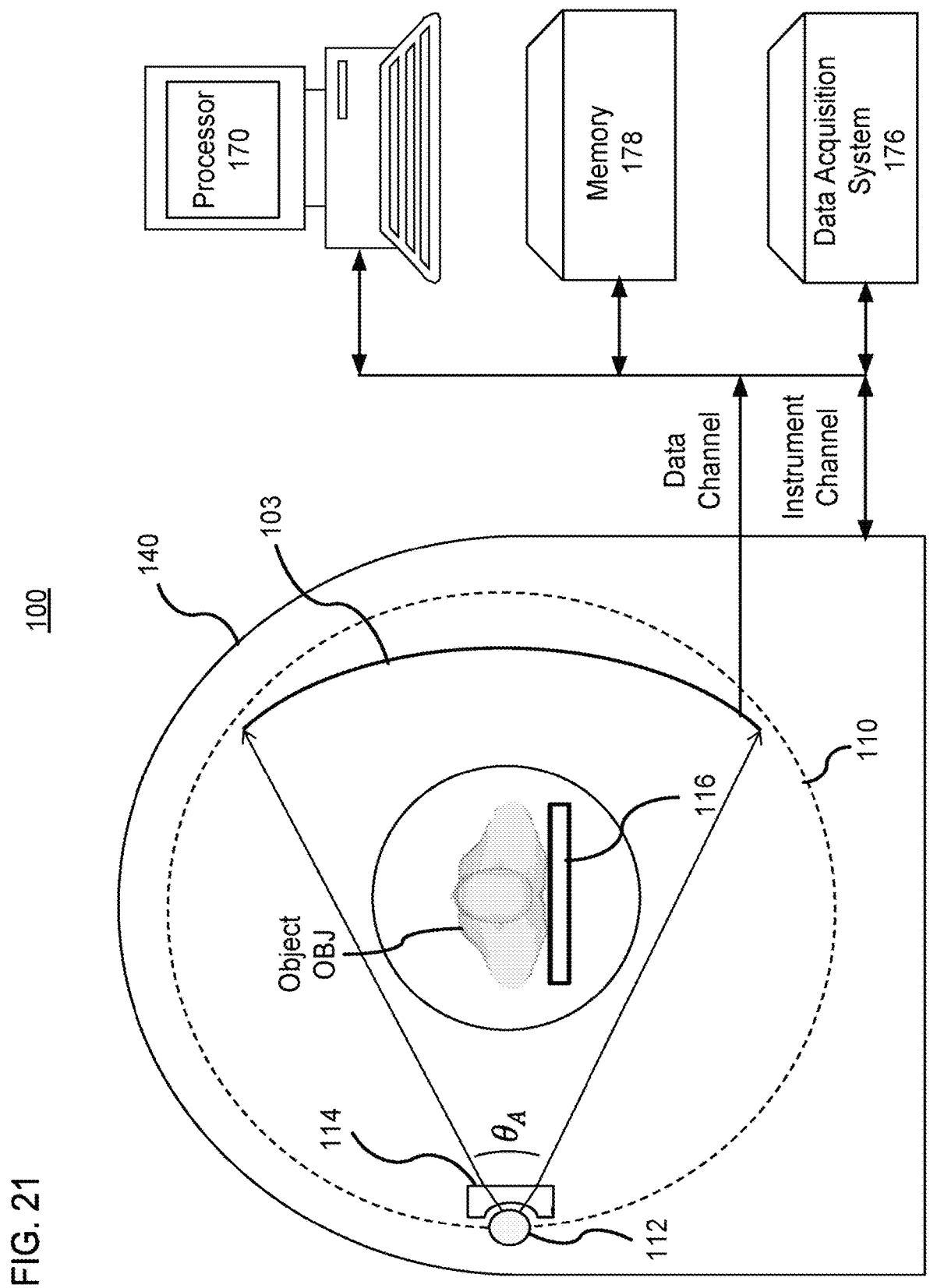
FIG. 21 shows a first example of computed tomography (CT) scanner for sparse kv-switching, according to one implementation.

FIG. 21 shows a first implementation of a computed tomography (CT) scanner having energy-integrating detectors arranged in a third-generation geometry. The diagram illustrates relative positions among the X-ray source 112, the collimator/filter 114, the X-ray detector 103, and the photon-counting detectors PCD1 through PCDN.

In addition to the configuration of the X-ray source 112 and the detector unit 103 shown in FIG. 21, other types and combinations of X-ray detectors and X-ray source can be used to obtain the projection data.

FIG. 21 also shows circuitry and hardware for acquiring, storing, processing, and distributing X-ray projection data. The circuitry and hardware include: a processor 170, a memory 178, and a data acquisition system 176.

As the X-ray source 112 and the detector unit 103 are housed in a gantry 140 and rotate around circular path of the rotational component 110. The detector elements in the detector unit 103 detect the X-ray radiation that has been transmitted and output the detected signals as the detector unit 103 rotates. In one implementation, the detector unit 103 has densely placed energy-integrating detectors in predetermined channel and segment directions on the detector unit surface.

In one implementation, the X-ray source 112 is optionally a single X-ray source that is configured to perform a kVp-switching function for emitting X-ray radiation at a predetermined high-level energy and at a predetermined low-level energy.

The detector unit 103 can use energy integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline, an organic liquid, a plastic, or other know scintillator.

The CT scanner also includes a data channel that routes projection measurement results from the photon-counting detectors and the detector unit 103 to a data acquisition system 176, a processor 170, and memory 178. The data acquisition system 176 controls the acquisition, digitization, and routing of projection data from the detectors. The data acquisition system 176 also includes radiography control circuitry to control the rotation of the annular rotating frames 110 and 130. In one implementation data acquisition system 176 will also control the movement of the bed 116, the operation of the X-ray source 112, and the operation of the X-ray detectors 103. The data acquisition system 176 can be a centralized system or alternatively it can be a distributed system. In an implementation, the data acquisition system 176 is integrated with the processor 170. The processor 170 performs functions including reconstructing images from the projection data, pre-reconstruction processing of the projection data, and post-reconstruction processing of the image data. The processor 170 also performs the functions and methods described herein.

The pre-reconstruction processing of the projection data can include correcting for detector calibrations, detector nonlinearities, polar effects, noise balancing, and material decomposition. Additionally, the pre-reconstruction processing can include various processing in step 210.

Post-reconstruction processing can include filtering and smoothing the image, volume rendering processing, and image difference processing as needed. Additionally, the Post-reconstruction processing can include steps from the various implementations method 200, including process 202, 310, 320, and 330.

The image-reconstruction process can be performed using filtered back-projection, iterative-image-reconstruction methods, or stochastic-image-reconstruction methods. Additionally, the image-reconstruction processing can include step 220.

Both the processor 170 and the data acquisition system 176 can make use of the memory 176 to store, e.g., projection data, reconstructed images, calibration data and parameters, and computer programs.

The processor 170 can include a CPU and a network controller. The CPU can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art. The network controller can be, e.g., an Intel Ethernet PRO network interface card from Intel Corporation of America, can interface between the various parts of the CT scanner. Additionally, the network controller can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

The memory 178 can be a hard disk drive, CD-ROM drive, DVD drive, FLASH drive, RAM, ROM or any other electronic storage known in the art.

Figure 22:
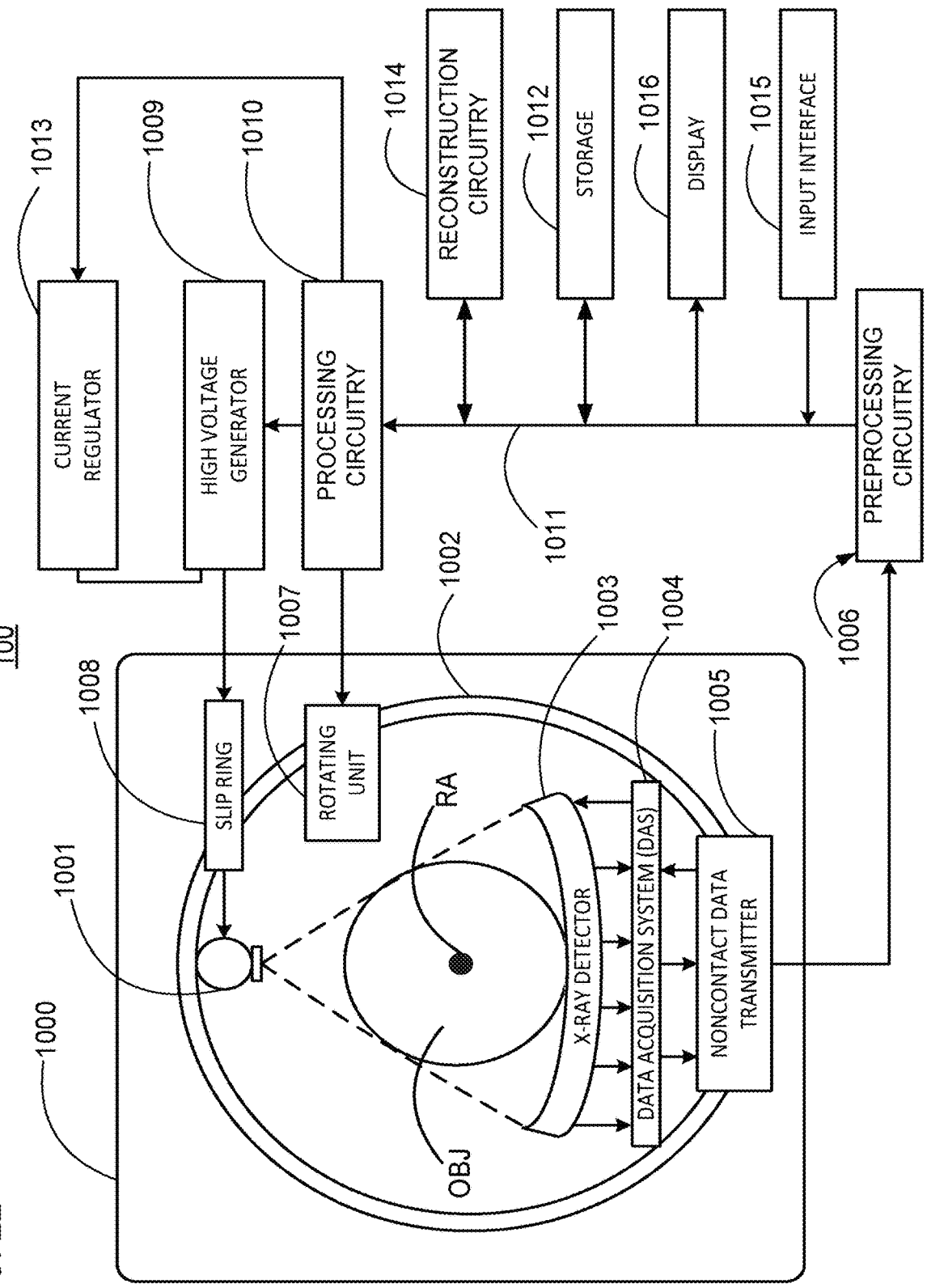
FIG. 22 shows a second example of CT scanner for sparse kv-switching, according to one implementation.

FIG. 22 illustrates a second implementation of the radiography gantry included in a CT apparatus or scanner 100. As shown in FIG. 22, a radiography gantry 1000 is illustrated from a side view and further includes an X-ray tube 1001, an annular frame 1002, and a multi-row or two-dimensional-array-type X-ray detector 1003. The X-ray tube 1001 and X-ray detector 1003 are diametrically mounted across an object OBJ on the annular frame 1002, which is rotatably supported around a rotation axis RA. A rotating unit 1007 rotates the annular frame 1002 at a high speed, such as 0.4 sec/rotation, while the object OBJ is being moved along the axis RA into or out of the illustrated page.

The first embodiment of an X-ray computed tomography (CT) apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, will be exemplified.

The multi-slice X-ray CT apparatus further includes a high voltage generator 1009 that generates a tube voltage applied to the X-ray tube 1001 through a slip ring 1008 so that the X-ray tube 1001 generates X-rays. The X-rays are emitted towards the object OBJ, whose cross sectional area is represented by a circle. For example, the X-ray tube 1001 having an average X-ray energy during a first scan that is less than an average X-ray energy during a second scan. Thus, two or more scans can be obtained corresponding to different X-ray energies. The X-ray detector 1003 is located at an opposite side from the X-ray tube 1001 across the object OBJ for detecting the emitted X-rays that have transmitted through the object OBJ. The X-ray detector 1003 further includes individual detector elements or units.

The CT apparatus further includes other devices for processing the detected signals from X-ray detector 1003. A data acquisition circuit or a Data Acquisition System (DAS) 1004 converts a signal output from the X-ray detector 1003 for each channel into a voltage signal, amplifies the signal, and further converts the signal into a digital signal. The X-ray detector 1003 and the DAS 1004 are configured to handle a predetermined total number of projections per rotation (TPPR).

The above-described data is sent to a preprocessing circuitry 1006, which is housed in a console outside the radiography gantry 1000 through a non-contact data transmitter 1005. The preprocessing circuitry 1006 performs certain corrections, such as sensitivity correction on the raw data. A storage 1012 stores the resultant data, which is also called projection data at a stage immediately before reconstruction processing. The storage 1012 is connected to a processing circuitry 1010 through a data/control bus 1011, together with a reconstruction device 1014, input interface 1015, and display 1016. The processing circuitry 1010 controls a current regulator 1013 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 1001 and the X-ray detector 1003 are diametrically mounted on the annular frame 1002 and are rotated around the object OBJ as the annular frame 1002 is rotated about the rotation axis RA. In the fourth-generation geometry system, the detectors are fixedly placed around the patient and an X-ray tube rotates around the patient. In an alternative embodiment, the radiography gantry 1000 has multiple detectors arranged on the annular frame 1002, which is supported by a C-arm and a stand.

The storage 1012 can store the measurement value representative of the irradiance of the X-rays at the X-ray detector unit 1003. Further, the storage 1012 can store a dedicated program for executing the methods described herein (e.g., method 200 and variations thereof).

The reconstruction circuitry 1014 can execute various steps of methods described herein (e.g., step 220 of method 200 and variations thereof). Further, reconstruction circuitry 1014 can execute pre-reconstruction processing image processing such as volume rendering processing and image difference processing as needed.

The pre-reconstruction processing of the projection data performed by the preprocessing circuitry 1006 can include correcting for detector calibrations, detector nonlinearities, and polar effects, for example. Further, the pre-reconstruction processing can include step 210.

Post-reconstruction processing performed by the reconstruction circuitry 1014 can include filtering and smoothing the image, volume rendering processing, and image difference processing as needed. The image reconstruction process can implement various steps of method 200 (e.g., steps 230, 230, and 250) and also the offline training of the DL-ANN networks (e.g., process 310, 320, and 330). The reconstruction circuitry 1014 can use the memory to store, e.g., projection data, reconstructed images, calibration data and parameters, and computer programs.

The reconstruction circuitry 1014 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the storage 1012 can be non-volatile, such as ROM, EPROM, EEPROM or FLASH memory. The storage 1012 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction circuitry 1014 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 1016. The display 1016 can be an LCD display, CRT display, plasma display, OLED, LED or any other display known in the art.

The storage 1012 can be a hard disk drive, CD-ROM drive, DVD drive, FLASH drive, RAM, ROM or any other electronic storage known in the art.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
processing circuitry configured to
obtain projection data representing an intensity of X-ray radiation at a plurality of detector elements, the projection data representing first sparse-view data acquired using a first voltage applied to an X-ray source and second sparse-view data acquired using a second voltage applied to the X-ray source, the second voltage being greater than the first voltage and the first sparse-view data being acquired at views that are different from views at which the second sparse-view data is acquired,
reconstruct, from the first sparse-view data, a first low-energy image,
reconstruct, from the second sparse-view data, a first high-energy image,
acquire an artifact-mitigating neural network that has two channels, one input channel for a low-energy image and another input channel for a high-energy image, the artifact-mitigating neural network having been trained using a training dataset that includes input images that are respective pairs of sparse-view reconstructed images that have complementary streak artifacts and corresponding target images in which the streak artifacts are mitigated, and
apply the first low-energy image and the first high-energy image to the artifact-mitigating neural network to generate artifact-mitigated images.

2. The apparatus according to claim 1, wherein the artifact-mitigated images include a second low-energy image and a second high-energy image, the second low-energy image representing the first low-energy image after mitigation of the streak artifacts, and the second high-energy image representing the first high-energy image after mitigation of the streak artifacts.

3. The apparatus according to claim 2, wherein the processing circuitry is further configured to
acquire a material-decomposition neural network that has two channels, one input channel for the low-energy image and another input channel for the high-energy image, the material-decomposition neural network having been trained to generate a first material image and a second material image when a pair of a low-energy image and a high-energy image, which have streak artifacts mitigated, are applied to the material decomposition neural network, and
apply the second low-energy image and the second high-energy image to the material-decomposition neural network to generate material-decomposed images.

4. The apparatus according to claim 3, wherein the processing circuitry is further configured to acquire the material-decomposition neural network, wherein the material-decomposition neural network has been trained using a training dataset in which material-decomposed target images include corrections for beam hardening and account for spatial variations in an X-ray beam used to generate the target images.

5. The apparatus according to claim 3, wherein the processing circuitry is further configured to acquire the material-decomposition neural network, wherein
the material-decomposition neural network has been trained using the training dataset in which the target images are training material-decomposed images that have been transformed using a whitening transform, and the generated material-decomposed images are generated by applying an inverse whitening transform to resultant images output from the material-decomposition neural network.

6. The apparatus according to claim 1, wherein the processing circuitry is further configured to acquire the artifact-mitigating neural network, wherein the artifact-mitigating neural network has been trained using a training dataset in which target images are generated based on first full-view projection data acquired using a low-energy X-ray beam and second full-view projection data acquired using a high-energy X-ray beam.

7. The apparatus according to claim 1, wherein the processing circuitry is further configured to acquire the artifact-mitigating neural network, wherein the artifact-mitigating neural network is also a material-decomposition neural network that has been trained to both mitigate streak artifacts and decompose spectral images into material components as an integrated process when sparse-view reconstructed images are applied to the artifact-mitigating neural network.

8. The apparatus according to claim 7, wherein the processing circuitry is further configured to acquire the artifact-mitigating neural network, wherein the artifact-mitigating neural network has been trained using a training dataset in which target images are material images decomposed from spectral images reconstructed from first full-view projection data acquired using a low-energy X-ray beam and from second full-view projection data acquired using a high-energy X-ray beam, and the input images are spectral images reconstructed from first sparse-view projection data acquired using the low-energy X-ray beam and from second sparse-view projection data acquired using the high-energy X-ray beam, the first sparse-view projection data being at projection views that are different angles than projection views of the second sparse-view projection data.

9. The apparatus according to claim 7, wherein the processing circuitry is further configured to acquire the artifact-mitigating neural network, wherein the artifact-mitigating neural network has been trained using the training dataset in which the target images are training material-decomposed images that have been transformed using a whitening transform, and the generated material-decomposed images are generated by applying an inverse whitening transform to resultant images output from the material-decomposition neural network.

10. The apparatus according to claim 1, wherein the processing circuitry is further configured to acquire the artifact-mitigating neural network, wherein the artifact-mitigating neural network has been trained using a training dataset in which the input images are reconstructed using a same reconstruction method as used to reconstruct the first low-energy image and the first high-energy image.

11. The apparatus according to claim 1, further comprising an X-ray source configured to radiate X-rays having an energy spectrum that depends on a voltage applied to the X-ray source, an energy-integrating X-ray detector having the plurality of detector elements configured to output the projection data, and control circuitry configured to rotate the X-ray source and the energy-integrating X-ray detector through a series of projection views, and change, back-and-forth between a high kilo-voltage and a low kilo-voltage, the voltage applied to the X-ray source at increments of two or more projection views of the series of projection views.

12. The apparatus according to claim 11, wherein the control circuitry is configured to change the voltage applied to the X-ray source such that a number of projection views at the high kilo-voltage is different from a number of projection views at the low kilo-voltage.

13. An apparatus, comprising:

processing circuitry configured to train an artifact-mitigating neural network having two channels by initializing the artifact-mitigating neural network, obtaining input images including pairs of sparse-view reconstructed images that have complementary streak artifacts, the sparse-view reconstructed images representing reconstructed images from projection data of a sparse-view kilo-voltage peak (kVp)-switching computed tomography (CT) scan, obtaining target images including pairs of images corresponding to the sparse-view reconstructed images except with the streak artifacts having been mitigated, and iteratively updating network coefficients to optimize a loss function representing agreement between the target images and output images resulting from the input images applied to the artifact-mitigating neural network.

14. The apparatus according to claim 13, wherein the processing circuitry is further configured to train the artifact-mitigating neural network, wherein the obtained target images include pairs of full-view reconstructed images that represent reconstructed images from projection data of a full-view kVp-switching CT scan.

15. The apparatus according to claim 13, wherein the processing circuitry is further configured to train the artifact-mitigating neural network, wherein the obtained target images include pairs of material component images generated by performing material decomposition on in the sinogram domain using projection data of a full-view kVp-switching CT scan to generate material-component projection data, and reconstructing material images from the material-component projection data.

16. The apparatus according to claim 15, wherein the processing circuitry is further configured to train the artifact-mitigating neural network, wherein the obtained target images further include that the pairs of material component images are generated by performing a whitening transform on the reconstructed material images.

17. A method of mitigating artifacts in computed tomography (CT) images from sparse-view kilo-voltage peak (kVp)-switching CT scans, comprising:

obtaining projection data representing an intensity of X-ray radiation at a plurality of detector elements, the projection data representing first sparse-view data acquired using a first voltage applied to an X-ray source and second sparse-view data acquired using a second voltage applied to the X-ray source, the second voltage being greater than the first voltage and the first sparse-view data being acquired at views that are different from views at which the second sparse-view data is acquired, reconstructing, from the first sparse-view data, a first low-energy image, reconstructing, from the second sparse-view data, a first high-energy image, acquiring an artifact-mitigating neural network that has two channels, one input channel for a low-energy image and another input channel for a high-energy image, and the artifact-mitigating neural network having been trained using a training dataset that includes input images that are respective pairs of sparse-view reconstructed images that have complementary streak artifacts and corresponding target images in which the streak artifacts are mitigated, and applying the first low-energy image and the first high-energy image to the artifact-mitigating neural network to generate artifact-mitigated images.

18. The method according to claim 17, wherein the artifact-mitigated images include a second low-energy image and a second high-energy image, the second low-energy image representing the first low-energy image after mitigation of the streak artifacts, and the second high-energy image representing the first high-energy image after mitigation of the streak artifacts, the method further comprising acquiring a material-decomposition neural network that has two channels, one input channel for a low-energy image and another input channel for a high-energy image, and the material-decomposition neural network having been trained to generate a first material image and a second material image when a pair of a low-energy image and a high-energy image, which have streak artifacts mitigated, are applied to the material decomposition neural network, and applying the second low-energy image and the second high-energy image to the material-decomposition neural network to generate material-decomposed images.

19. The method according to claim 18, wherein the acquiring of the artifact-mitigating neural network further includes that the artifact-mitigating neural network is also a material-decomposition neural network that has been configured to both mitigate streak artifacts and decompose spectral images into material components as an integrated process when sparse-view reconstructed images are applied to the artifact-mitigating neural network.

20. A non-transitory computer readable storage medium including executable instructions, wherein the instructions, when executed by circuitry, cause the circuitry to perform the method according to claim 17.

* * * * *